US009410155B2

(12) United States Patent
Collard et al.

(10) Patent No.: US 9,410,155 B2
(45) Date of Patent: Aug. 9, 2016

(54) TREATMENT OF VASCULAR ENDOTHELIAL GROWTH FACTOR (VEGF) RELATED DISEASES BY INHIBITION OF NATURAL ANTISENSE TRANSCRIPT TO VEGF

(71) Applicant: CuRNA, Inc., Miami, FL (US)

(72) Inventors: Joseph Collard, Delray Beach, FL (US); Olga Khorkova Sherman, Tequesta, FL (US)

(73) Assignee: CuRNA, Inc., Miami, FL (US)

( * ) Notice: Subject to any disclaimer, the term of this patent is extended or adjusted under 35 U.S.C. 154(b) by 0 days.

(21) Appl. No.: 14/534,349

(22) Filed: Nov. 6, 2014

(65) Prior Publication Data
US 2015/0141494 A1    May 21, 2015

Related U.S. Application Data

(62) Division of application No. 13/132,997, filed as application No. PCT/US2009/066455 on Dec. 2, 2009, now Pat. No. 8,927,511.

(60) Provisional application No. 61/119,957, filed on Dec. 4, 2008.

(51) Int. Cl.
C07H 21/04 (2006.01)
C12N 15/113 (2010.01)
A61K 31/712 (2006.01)
C12Q 1/68 (2006.01)

(52) U.S. Cl.
CPC .......... *C12N 15/1136* (2013.01); *A61K 31/712* (2013.01); *C12Q 1/6816* (2013.01); *C12Q 1/6883* (2013.01); *C12Q 1/6886* (2013.01); *C12N 2310/11* (2013.01); *C12N 2310/113* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,754,065 A | 6/1988 | Levenson et al. |
| 4,800,159 A | 1/1989 | Mullis et al. |
| 5,034,506 A | 7/1991 | Summerton et al. |
| 5,138,045 A | 8/1992 | Cook et al. |
| 5,218,105 A | 6/1993 | Cook et al. |
| 5,288,512 A | 2/1994 | Seiden |
| 5,288,514 A | 2/1994 | Ellman |
| 5,319,080 A | 6/1994 | Leumann |
| 5,393,878 A | 2/1995 | Leumann |
| 5,432,272 A | 7/1995 | Benner et al. |
| 5,457,189 A | 10/1995 | Crooke et al. |
| 5,459,255 A | 10/1995 | Cook et al. |
| 5,474,796 A | 12/1995 | Brennan |
| 5,491,084 A | 2/1996 | Chalfie et al. |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,549,974 A | 8/1996 | Holmes |
| 5,569,588 A | 10/1996 | Ashby et al. |
| 5,576,302 A | 11/1996 | Cook et al. |
| 5,593,853 A | 1/1997 | Chen et al. |
| 5,605,662 A | 2/1997 | Heller et al. |
| 5,661,134 A | 8/1997 | Cook et al. |
| 5,708,161 A | 1/1998 | Reese |
| 5,736,294 A * | 4/1998 | Ecker et al. ................. 435/375 |
| 5,739,119 A | 4/1998 | Galli et al. |
| 5,739,311 A | 4/1998 | Lackey et al. |
| 5,756,710 A | 5/1998 | Stein et al. |
| 5,849,902 A | 12/1998 | Arrow et al. |
| 5,891,725 A | 4/1999 | Soreq et al. |
| 5,902,880 A | 5/1999 | Thompson |
| 5,908,779 A | 6/1999 | Carmichael et al. |
| 5,965,721 A | 10/1999 | Cook et al. |
| 5,985,663 A | 11/1999 | Bennett et al. |
| 6,005,095 A | 12/1999 | Capaccioli et al. |
| 6,013,639 A | 1/2000 | Peyman et al. |
| 6,013,786 A | 1/2000 | Chen et al. |
| 6,034,233 A | 3/2000 | Ecker et al. |
| 6,100,090 A | 8/2000 | Monia et al. |
| 6,140,492 A | 10/2000 | Morelli et al. |
| 6,147,200 A | 11/2000 | Manoharan et al. |
| 6,165,712 A | 12/2000 | Foulkes et al. |
| 6,165,990 A | 12/2000 | Singh et al. |
| 6,175,409 B1 | 1/2001 | Nielsen et al. |
| 6,221,587 B1 | 4/2001 | Ecker et al. |
| 6,239,265 B1 | 5/2001 | Cook |
| 6,242,589 B1 | 6/2001 | Cook et al. |
| 6,268,490 B1 | 7/2001 | Imanishi et al. |
| 6,303,374 B1 | 10/2001 | Zhang et al. |
| 6,307,040 B1 | 10/2001 | Cook et al. |

(Continued)

FOREIGN PATENT DOCUMENTS

CA    2686933    4/2008
EP    335451 A3    3/1988

(Continued)

OTHER PUBLICATIONS

Nikiforov et al. (PCR Methods and Applications 1994: 285-291).*

(Continued)

*Primary Examiner* — Kimberly Chong
(74) *Attorney, Agent, or Firm* — CuRNA, Inc.; Monte R. Browder

(57) ABSTRACT

Oligonucleotide compounds modulate expression and/or function of Vascular Endothelial Growth Factor (VEGF) polynucleotides and encoded products thereof. Methods for treating diseases associated with Vascular Endothelial Growth Factor (VEGF) comprise administering one or more Oligonucleotide compounds designed to inhibit the VEGF natural antisense transcript to patients.

12 Claims, 9 Drawing Sheets

(56) References Cited

U.S. PATENT DOCUMENTS

| | | |
|---|---|---|
| 6,316,198 B1 | 11/2001 | Skouv et al. |
| 6,335,434 B1 | 1/2002 | Guzaev et al. |
| 6,376,541 B1 | 4/2002 | Nixon et al. |
| 6,403,566 B1 | 6/2002 | Wang |
| 6,444,464 B1 | 9/2002 | Wyatt |
| 6,451,991 B1 | 9/2002 | Martin et al. |
| 6,525,191 B1 | 2/2003 | Ramassamy |
| 6,528,262 B1 | 3/2003 | Gilad et al. |
| 6,528,631 B1 | 3/2003 | Cook et al. |
| 6,617,122 B1 | 9/2003 | Hayden et al. |
| 6,617,442 B1 | 9/2003 | Crooke et al. |
| 6,630,315 B1 | 10/2003 | Miwa et al. |
| 6,639,059 B1 | 10/2003 | Kochkine et al. |
| 6,656,730 B1 | 12/2003 | Manoharan |
| 6,667,337 B2 | 12/2003 | Wilson |
| 6,670,461 B1 | 12/2003 | Wengel et al. |
| 6,710,174 B2 | 3/2004 | Bennett et al. |
| 6,734,291 B2 | 5/2004 | Kochkine et al. |
| 6,762,169 B1 | 7/2004 | Manoharan |
| 6,794,499 B2 | 9/2004 | Wengel et al. |
| 6,833,361 B2 | 12/2004 | Hong et al. |
| 6,861,514 B2 | 3/2005 | Cook et al. |
| 6,867,294 B1 | 3/2005 | Sanghvi et al. |
| 6,936,467 B2 | 8/2005 | Kmiec et al. |
| 6,936,593 B1 | 8/2005 | Agrawal et al. |
| 6,977,295 B2 | 12/2005 | Belotserkovskii et al. |
| 6,986,988 B2 | 1/2006 | Gilad et al. |
| 7,034,133 B2 | 4/2006 | Wengel et al. |
| 7,034,145 B2 | 4/2006 | Shen et al. |
| 7,053,195 B1 | 5/2006 | Goff |
| 7,053,199 B2 | 5/2006 | Imanishi et al. |
| 7,053,207 B2 | 5/2006 | Wengel |
| 7,060,809 B2 | 6/2006 | Wengel et al. |
| 7,084,125 B2 | 8/2006 | Wengel |
| 7,087,589 B2 | 8/2006 | Jacobson et al. |
| 7,125,982 B1 | 10/2006 | Frayne |
| 7,144,995 B2 | 12/2006 | Wise et al. |
| 7,144,999 B2 | 12/2006 | Ward et al. |
| 7,148,204 B2 | 12/2006 | Bennett et al. |
| 7,153,954 B2 | 12/2006 | Koch et al. |
| 7,169,916 B2 | 1/2007 | Krotz et al. |
| 7,199,107 B2 | 4/2007 | Dobie et al. |
| 7,202,357 B2 | 4/2007 | Crooke et al. |
| 7,217,572 B2 | 5/2007 | Ward et al. |
| 7,220,549 B2 | 5/2007 | Buzby |
| 7,226,785 B2 | 6/2007 | Kmiec et al. |
| 7,229,974 B2 | 6/2007 | Peyman et al. |
| 7,229,976 B2 | 6/2007 | Dobie et al. |
| 7,235,534 B2 | 6/2007 | Tauguay et al. |
| 7,235,653 B2 | 6/2007 | Bennett et al. |
| 7,238,858 B2 | 7/2007 | Marraccini et al. |
| 7,250,289 B2 * | 7/2007 | Zhou .................. 435/287.2 |
| 7,276,599 B2 | 10/2007 | Moore et al. |
| 7,285,288 B1 | 10/2007 | Tormo et al. |
| 7,297,786 B2 | 11/2007 | McCray et al. |
| 7,314,923 B2 | 1/2008 | Kaneko et al. |
| 7,320,965 B2 | 1/2008 | Sah et al. |
| 7,321,828 B2 | 1/2008 | Cowsert et al. |
| 7,335,764 B2 | 2/2008 | Crooke et al. |
| 7,335,765 B2 | 2/2008 | Kaneko et al. |
| 7,339,051 B2 | 3/2008 | Crooke et al. |
| 7,371,833 B1 | 5/2008 | Weiss |
| 7,399,845 B2 | 7/2008 | Seth et al. |
| 7,402,434 B2 | 7/2008 | Newman et al. |
| 7,402,574 B2 | 7/2008 | Iversen et al. |
| 7,420,050 B2 | 9/2008 | Park et al. |
| 7,423,142 B2 | 9/2008 | Vornlocher |
| 7,425,545 B2 | 9/2008 | Crooke et al. |
| 7,427,675 B2 | 9/2008 | Capaldi et al. |
| 7,456,154 B2 | 11/2008 | Soreq et al. |
| 7,462,642 B2 | 12/2008 | Wang et al. |
| 7,468,431 B2 | 12/2008 | Bhanot et al. |
| 7,510,830 B2 | 3/2009 | Baguley et al. |
| 7,541,344 B2 | 6/2009 | Bhat et al. |
| 7,547,684 B2 | 6/2009 | Seth et al. |
| 7,569,575 B2 | 8/2009 | Sorensen et al. |
| 7,569,686 B1 | 8/2009 | Bhat et al. |
| 7,572,582 B2 | 8/2009 | Wengel et al. |
| 7,582,745 B2 | 9/2009 | Sah et al. |
| 7,585,893 B2 | 9/2009 | Baguley et al. |
| 7,589,190 B2 | 9/2009 | Westergaard et al. |
| 7,598,227 B2 | 10/2009 | Crooke et al. |
| 7,605,251 B2 | 10/2009 | Tan et al. |
| 7,622,453 B2 | 11/2009 | Frieden et al. |
| 7,662,948 B2 | 2/2010 | Kurreck et al. |
| 7,666,854 B2 | 2/2010 | Seth et al. |
| 7,674,895 B2 | 3/2010 | Reich et al. |
| 7,687,617 B2 | 3/2010 | Thrue et al. |
| 7,691,995 B2 | 4/2010 | Zamore et al. |
| 7,695,902 B2 | 4/2010 | Crooke |
| 7,696,345 B2 | 4/2010 | Allerson et al. |
| 7,709,456 B2 | 5/2010 | Corey et al. |
| 7,709,630 B2 | 5/2010 | Gaarde et al. |
| 7,713,738 B2 | 5/2010 | Hansen et al. |
| 7,718,629 B2 | 5/2010 | Bamcrot et al. |
| 7,723,508 B2 | 5/2010 | Crooke et al. |
| 7,732,422 B2 | 6/2010 | Gleave et al. |
| 7,732,590 B2 | 6/2010 | Bhanot et al. |
| 7,737,264 B2 | 6/2010 | Thrue et al. |
| 7,737,265 B2 | 6/2010 | Akinc et al. |
| 7,741,305 B2 | 6/2010 | Crooke et al. |
| 7,741,309 B2 | 6/2010 | Hansen et al. |
| 7,741,457 B2 | 6/2010 | Seth et al. |
| 7,745,609 B2 | 6/2010 | Bennett et al. |
| 7,749,978 B2 | 7/2010 | Sah et al. |
| 2003/0139359 A1 | 7/2003 | Dobie |
| 2003/0186920 A1 | 10/2003 | Sirois |
| 2003/0191075 A1 | 10/2003 | Cook et al. |
| 2003/0228618 A1 | 12/2003 | Levanon et al. |
| 2003/0233670 A1 | 12/2003 | Edgerton et al. |
| 2004/0006031 A1 | 1/2004 | Dean et al. |
| 2004/0033480 A1 | 2/2004 | Wong |
| 2004/0101858 A1 | 5/2004 | Ward et al. |
| 2004/0137423 A1 | 7/2004 | Hayden et al. |
| 2004/0138155 A1 | 7/2004 | Baird et al. |
| 2004/0175803 A1 | 9/2004 | Meritet et al. |
| 2004/0180336 A1 | 9/2004 | Gilad et al. |
| 2004/0254137 A1 | 12/2004 | Ackermann et al. |
| 2005/0009771 A1 | 1/2005 | Levanon et al. |
| 2005/0026160 A1 | 2/2005 | Allerson et al. |
| 2005/0113326 A1 | 5/2005 | Siwkowski et al. |
| 2005/0143357 A1 | 6/2005 | Pousette et al. |
| 2005/0153286 A1 | 7/2005 | Clements |
| 2005/0215504 A1 | 9/2005 | Bennett et al. |
| 2005/0222029 A1 | 10/2005 | Bartel et al. |
| 2006/0009410 A1 | 1/2006 | Crooke et al. |
| 2006/0142196 A1 | 6/2006 | Klein et al. |
| 2006/0178333 A1 | 8/2006 | Soreq et al. |
| 2007/0082848 A1 | 4/2007 | Alitalo et al. |
| 2007/0197459 A1 | 8/2007 | Milner |
| 2007/0213274 A1 | 9/2007 | Salonen |
| 2007/0213292 A1 | 9/2007 | Stoffel et al. |
| 2007/0231816 A1 | 10/2007 | Chaussabel et al. |
| 2007/0248590 A1 | 10/2007 | Milne et al. |
| 2008/0146788 A1 | 6/2008 | Bhat et al. |
| 2008/0221051 A1 | 9/2008 | Becker et al. |
| 2008/0293142 A1 | 11/2008 | Liu et al. |
| 2009/0191263 A1 | 7/2009 | Reich et al. |
| 2009/0192106 A1 | 7/2009 | Dobie et al. |
| 2009/0208479 A1 | 8/2009 | Jaye et al. |
| 2009/0258925 A1 | 10/2009 | Wahlestedt |
| 2009/0318536 A1 | 12/2009 | Freier et al. |
| 2009/0326041 A1 | 12/2009 | Bhanot et al. |
| 2010/0105760 A1 | 4/2010 | Collard et al. |

FOREIGN PATENT DOCUMENTS

| | | |
|---|---|---|
| EP | 335451 A2 | 10/1989 |
| WO | WO-84/03504 | 9/1984 |
| WO | WO-91/19735 | 12/1991 |
| WO | WO-92/00091 | 1/1992 |
| WO | WO-92/08796 | 5/1992 |
| WO | WO-93/20242 | 10/1993 |
| WO | WO-94/26887 A1 | 11/1994 |

(56) References Cited

FOREIGN PATENT DOCUMENTS

| WO | WO-94/28143 | 12/1994 |
|---|---|---|
| WO | WO-95-15373 A2 | 6/1995 |
| WO | WO-95/22618 | 8/1995 |
| WO | WO-95/25116 | 10/1995 |
| WO | WO-95/35505 | 12/1995 |
| WO | WO-96-27663 A2 | 9/1996 |
| WO | WO-97-39120 A1 | 10/1997 |
| WO | WO-99-14226 A1 | 3/1999 |
| WO | WO-99-39352 A1 | 8/1999 |
| WO | WO-00-57837 A1 | 10/2000 |
| WO | WO-00-61770 A2 | 10/2000 |
| WO | WO-01-00669 A2 | 1/2001 |
| WO | WO-01-21631 A2 | 3/2001 |
| WO | WO-01-25488 A2 | 4/2001 |
| WO | WO-01-51630 A1 | 7/2001 |
| WO | WO-02-062840 A1 | 8/2002 |
| WO | WO-02-068688 A1 | 9/2002 |
| WO | WO-2004-016255 A1 | 2/2004 |
| WO | WO-2004-024079 A2 | 3/2004 |
| WO | WO-2004-030750 A1 | 4/2004 |
| WO | WO-2004-041838 A1 | 5/2004 |
| WO | WO-2004-104161 A2 | 12/2004 |
| WO | WO-2005-045034 A2 | 5/2005 |
| WO | WO-2005-070136 A2 | 8/2005 |
| WO | WO-2005-079862 A1 | 9/2005 |
| WO | WO-2007-028065 A2 | 3/2007 |
| WO | WO-2007-071182 A1 | 6/2007 |
| WO | WO-2007-087113 A2 | 8/2007 |
| WO | WO 2007-138023 A1 | 12/2007 |
| WO | WO-2008-057556 A2 | 5/2008 |
| WO | WO-2008-066672 A2 | 6/2008 |
| WO | WO-2008-087561 A2 | 7/2008 |
| WO | WO 2010-002984 A1 | 1/2010 |
| WO | WO-2010-040571 A2 | 4/2010 |
| WO | WO-2010-054364 A1 | 5/2010 |
| WO | WO-2010-058227 A2 | 5/2010 |

OTHER PUBLICATIONS

Ausubel, Cnrreat Protocols in Molecular Biology vol. 1, 1994. 6.0.1-6.4.10.
Barak, et al., "A β-Arrestin/Green Fluorescent Protein Biosensor for Detecting G Protein-Coupled Receptor Activation," J. Biol. Chem. 272:27497-27500 (1997).
Barber, et al., "Delivery of membrane-impermeant fluorescent probes into living neural cell populations by lipotransfer," Neuroscience Letters 207:17-20 (1996).
Baum, "Solid-phase synthesis or benzodiazepines," C&EN News, Jan. 18, p. 33-34 (1993).
Bernstein, E., et al., "Role for a Bidentate Ribonuclease in the Initiation Step of RNA Interference," Nature 409:363-366 (2001).
Boutla, A., et al., "Short 5'-phosphorylated double-stranded RNAs induce RNA interference in *Drosophila*," Curr. Biol. 11:1776-1780 (2001).
Boyd-Kimball, et al., "Proteomic Identification of Proteins Specifically Oxidized by Intracerebral Injection of Amyloid β-Peptide (1-42) into Rat Brain: Implications for Alzheimer's Disease," Neuroscience 132, 313-324 (2005).
Brazma & Vilo, "Gene expression data analysis," FEBS Lett., 480:17-24 (2000).
Bright, et. al,. "Chapter 6. Fluorescence Ratio Imaging Microscopy," Methods in Cell Biology vol. 30, Taylor and Wang (eds) p. 157-192 (1989).
Bright, et al., "Delivery of Macromolecules Into Adherent Cells via Electroporation for Use in Fluorescence Spectroscopic Imaging and Metabolic Studies," Cytometry 24:226-233 (1996).
Bright, et al., "Fluorescence Ratio Imaging Microscopy: Temporal and Spatial Measurements of Cytoplasmic pH," J. Cell Biology 104:1019-1033 (1987).
Campbell, et al., "Phosphonmate Ester Synthesis Using a Modified Mitsunobu Condensation," J. Org. Chem. 59:658-660 (1994).
Caplen, N. J., et al., "Specific inhibition of gene expression by small double-stranded RNAs in invertebrate and vertebrate systems." PNAS Sci. USA 98:9742-9747 (2001).
Carninci, et al., "The transcriptional landscape of the mammalian genome," Science 309:1559-1563 (2005).
Carulli, et al., "High Throughput Analysis of Differential Gene Expression," J. Cell Biochem. Suppl., 3:286-296 (1998).
Celis, et al., "Gene expression profiling: monitoring transcription and translation products using DNA microarrays and proteomics," FEBS Lett., 480:2-16 (2000).
Chabala, J.C., "Solid-phase combinatorial chemistry and novel tagging methods for identifying leads," Curr Opin Biotechnol. 6:632-639 (1995).
Cech. J., "Ribozymes and Their Medical Implications," American. Med Assoc. 260:3030-3035 (1988).
Chen, et al., "Expression of ssDNA in Mammalian Cells," BioTechniques 34:167-171 (2003).
Chen, et al., "Analogous Organic Synthesis of Small-Compound Libraries: Validation of Combinatorial Chemistry in Small-Molecule Synthesis," J. Amer. Chem. Soc. 116:2661-2662 (1994).
Cheng, J. et al., "Transcriptional maps of 10 human chromosomes at 5-nucleotide resolution," Science 308:5725:1149-1154 (2005).
Cho, et al., "An Unnatural Biopolymer," Science 261:1303-1305 (1993).
Christiensen, N.K. et al., "A Novel Class of Oligonucleotide Analogues Containing 2'-O,3'-C-Linked [3.2.0]Bicycloarabinonucleoside Monomers: Synthesis, Thermal Affinity Studies, and Molecular Modeling," J. Am. Chem. Soc., 120:5458-5463 (1998).
Cubitt, et al. , "Understanding, improving and using green fluorescent proteins," Trends in Biochemical Science 20:448-455 (1995).
Curiel, D. T. et al., "Adenoviris enhancement of transferrin-polylysine-mediated gene delivery," PNAS 88:8850-8854 (1991).
Dai et al., "SIRT1 Interacts With p73 and Suppresses p73-Dependent Transcriptional Activity:" J Cell Physiol 210(1):161-165 (2007).
Davidson, et al., "A model system for in vivo gene transfer into the central nervous system using an adenoviral vector," Nat. Genet 3:219-223 (1993).
Davis, et al., "Direct Gene Transfer into Skeletal Muscle In Vivo: Factors Affecting Efficiency of Transfer and Stability of Expression," Hum Gene Ther 4:151-159 (1993).
De Mesmaeker, et al., "Antisense Oligonucleotides," Acc. Chem. Res. 28:366-374 (1995).
Deng et al., "Small Interfering RNA Targeting the PINK1 Induces Apoptosis in Dopaminergic Cells SH-SY5Y", Biochemical and Biophysical Research Communications, vol. 337, No. 4, pp. 1133-1138 (2005).
Dixon, et al., "Anthrax," New England J. Med. 341:815-826 (1999).
Dolle, "Discovery of Enzyme inhibitors through combinatorial chemistry," Mol Divers. 2:223-236 (1997).
Dykxhoorn, D., et al., "Determinants of Specific RNA Interference-Mediated Silencing of Human β-Globin Alleles Differing by a Single Nucleotide Polymorphism," PNAS, vol. 103, No. 15, pp. 5953-5958, (2006).
Eguchi, et al., "Antisense RNA." Annu. Rev. Biochem 60:631-652 (1991).
Eichler, et al., "Generation and utilization of synthetic combinatorial libraries," Mol Med Today 1:174-180 (1995).
Eichler, et al., "Peptide Peptidomimetic and organic synthetic combinatorial libraries," Med Res Rev 15:481-496 (1995).
Espeseth, et al., A genome wide analysis of ubiquitin ligases in APP processing identifies a novel regulator of BACE1 mRNA levels, Mol. Cell Neurosci. 33: 227-235 (2006).
Faghihi, M. & Wahlestedt, C., "RNA interference is not involved in natural antisense mediated regulation of gene expression in mammals," Genome Biol (2005).
Fauchere, et al., "Peptide and nonpeptide lead discovery using robotically synthesized soluble libraries," Can J. Physiol Pharmacol 75:683-689 (1997).
Felgner and Holm, "Cationic Liposome-Mediated Transfection," Bethesda Res. Lab Focus, 11:2:21 (1989).
Fields, et al., "How many genes in the human genome?" Nature Genetics 7:345-346 (1994).

(56) References Cited

OTHER PUBLICATIONS

Freier & Altman, "The ups and downs of nucleic acid duplex stability: structure-stability studies on chemically-modified DNA:RNA duplexes," Nucl. Acid Res., 25:22:4429-4443 (1997).
Fuchs, et al., "Identification of Differentially Expressed Genes by Mutually Subtracted RNA Fingerprinting," Anal. Biochem., 286:91-98 (2000).
Gebeyehu, G., et al., "Novel biotinylated nucleotide-analogs for labeling and colorimetric detection of DNA," Nucl. Acids Res. 15:4513 (1987).
Geller, A.I. et al., "An HSV-1 Vector Expressing Tyrosine Hydroxylase Causes Production and Release of L-DOPA from Cultured Rat Striatal Cells," J. Neurochem 64:487-496 (1995).
Geller, A.I. et al., "Long-term increases in neurotransmitter release from neuronal cells expressing a constitutively active adenylate cyclase from a herpes simplex virus type 1 vector," PNAS U.S.A. :90:7603-7607 (1993).
Geller, A.I., et al., "Infection of cultured central nervous system neurons with a defective herpes simplex virus 1 vector results in stable expression of *Escherichia coli* β-galactosidase," PNAS USA 87:1149-1153 (1990).
GenBank Accession No. NM_000559, *Homo sapiens* Hemoglobin, Gamma A (HBG1), mRNA, (2008).
Giuliano, et al., "FLuorescent Protein Biosensors: Measurement of Molecular Dynamics in Living Cells," Ann. Rev. of Biophysics and Biomolecular Structure. 24:405-434(1999).
Giuliano, et al., "Light-Optical-Based Reagents for the Measurement and Manipulation of Ions, Metabolites, and Macromolecules in Living Cells," Methods in Neuroscience 27:1-16 (1995).
Giuliano, et al., "Determination of Intracellular pH of BALB/c-3T3 Cells Using the Fluorescence of Pyranine," Anal. Biochem 167:362-371 (1987).
Going & Gusterson, "Molecular Pathology and Future Developments," Eur. J. Cancer, 35:1895-1904 (1999).
Hagihara, et al., "Vinylogous Polypeptides: An Alternate Peptide Backbone," J. Amer. Chem. Soc. 114:6568-6571 (1992).
Haussecker, D, et al., "Dicer-Dependent Turnover of Intergenic from the Human β-Globin Gene Cluster," Molecular and Cellular Biology, vol. 25, No. 21, pp: 9724-9793, (2005).
Heller, et al., "Discovery and analysis of inflammatory disease-related genes using cDNA microarrays," PNAS U.S.A. 94:2150-2155 (1997).
Herdewijn P., "Heterocyclic Modifications of Oligonucleotides and Antisense Technology," AntiSense & Nucleic Acid Drug Dev., 10:297-310 (2000).
Hirschmann, et al., J. Amer. Chem. Soc., 114:9217-9218 (1992).
Hobbs-DeWitt, et al., "Diversomers: An approach to nonpeptide, nonoligomeric chemical diversity," Proc. Nat. Acad. Sci. USA 90:6909-6913 (1993).
Houghton AN, Gold JS, Blachere NE, Immunity against cancer: lessons learned from melanoma,. Curr Opin Immunol 13:134-140 (2001).
International Human Genome Sequencing Consortium "Finishing the euchromatic sequence of the human genome." Nature 431:7011:931-945 (2004).
Janda, K.D. "Tagged versus untagged libraries: Methods for the generation and screening of combinatorial chemical libraries," PNAS 91:10779-10785 (1994).
Janowski, et al., "Inhibiting gene expression at transcription start sites in chromosomal DNA with antigene RNAs," Nature Chemical Biology, 1(4):216-222 (2005).
Jungblut, et al., "Proteomics in human disimse: Cancer, heart and infectious diseases," Electrophoresis 20:2100-2110 (1999).
Jurecic & Belmont, "Long-distance DD-PCR and cDNA microarrays," Curr. Opin, Microbiol., 3:316-321 (2000).
Kabanov, et al., "A new class of antivirals: antisense oligonueleotides combined with a hydrophobic substituent effectively inhibit influenza virus reproduction and synthesis of virus-specific proteins in MDCK cells," FEBS Lett. 259:327-330 (1990).

Kaplitt, M.G., et al., "Long-term gene expression and phenotypic correction using adeno-associated virus vectors in the mammalian brain," Nat. Genet, 8:148-154 (1994).
Kapranov, P. et al., "Examples of the complex architecture of the human transcriptome revealed by RACE and high-density tiling arrays," Genome Res 15:7:987-997 (2005).
Katayama, S. et al., "Antisense Transcription in the Mammalian Transcriptome," Science 309:1564-1566 (2005).
Kawahara & Nishikura, "Extensive adenosine-to-inosine editing detected in Alu repeats of antisense RNAs reveals scarcity of sense-antisense duplex formation," FEBS Lett 580:2301-2305 (2006).
Kay, et al., "Identification of enzyme inhibitors from phage-displayed combinatorial peptide libraries," Comb Chem High Throughput Screen 4:535-543 (2001).
Kenan, et al., "Exploriug molecular diversity wiih combinatorial shape libraries," Trends Biochem Sci 19:57-64 (1994).
Kornberg, A., DNA Replication, W.H. Freeman & Co., San Francisco, 1980 pp. 75-77.
Larson, et al., "Rapid DNA Fingerprinting of Pathogens by Flow Cytometry," Cytometry, 2000, 41:203-208 (2000).
Larsson, et al., "High-throughput protein expression of cDNA products as a tool in functional genomics," J. Biotechnology., 80:143-157 (2000).
Lebl, et al., "One-bead-one-structure combinatorial libraries," Biopolymers 37:177-198 (1995).
LeGAL Lasalle et al., "An Adenovirus Vector for Gene Transfer into Neurons and Glia in teh Brain," Science 259:988-990 (1993).
Letsinger, et al., "Cholesteryl-conjugated oligonucleotides: Synthesis, properties, and activity as inhibitors of replication of human immunodeficiency virus in cell culture," PNAS 86:6553-6556 (1989).
Li et al., "Control of APP processing and Aβ generation level by BACE1 enzymatic activity and transcription," Faseb J 20; 285-292 (2006).
Li, et al., J. Neurochem 89 1308-1312 (2004).
Liang, et al., "Parallel Synthesis and Screening of a Solid Phase Carbohydrate Library," Science 274:1520-1522 (1996).
Luther, "Role of endogenous antisense RNA in cardiac gene regulation," J. Mol. Med. 83:26-32 (2005).
Madden, et al., "Serial analysis of gene expression: from gene discovery to target identification," Drug Discov. Today 5:415-425 (2000).
Makalowska I, Lin CF, Makalowski W., "Overlapping genes in vertebrate genomes," Comput Biol. Chem 29:1:1-12 (2005).
Mannino and Gould-Fogerite, "Liposome Mediated Gene Transfer," BioTechniques 6:682-690 (1988).
Manoharan et al., "Lipidic Nucleic Acids," Tetrahedron Lett 36:3651-3654 (1995).
Manoharan, et al., "Chemical Modifications to Improve Uptake and Bioavailability of Antisense Oligonucleotides," Ann. N.Y. Acad. Scie 660:306-309 (1992).
Manoharan, et al., "Introduction of a Lipophilic Thioether in teh Minor Groove of Nucleic Acids for Antisense Applications," Bioorg. Med. Chem. Let 3:2765-2770 (1993).
Manoharan, et al., "Cholic Acid-Oligonucleotide Conjugates for Antisense Applications," Bioorg. Med. Chem. Let 4;1053 (1994).
Manoharan, et al., "Oligonucleotide Conjugates: Alteration of the Pharmacokinetic Properties of AntiSense Agents," Nucleosides & Nucleotides 14:969-973 (1995).
Manoharan, M., "2'-Carbohydrate modifications in antisense of oligonucleotide therapy: importance of conformation, configurationj and conjugation," Biochemica et Biophysica Acta 1489:117-139 (1999).
Mattick, J. S. "RNA reegulation: a new genetics?" Nat. Rev. Genet 5:4:316-323 (2004).
Maurer, R.A., "Cationic Liposome-Mediated Transfection of Primary Cultures of Rat Pituitary Cells," Bethesda Res. Lab. Focus 11:2:25 (1989).
McNeil in Methods in Cell Biology vol. 29, Taylor and Wang (eds.) p. 153-173 (1989).
Morelli et al., "The antisense*bcl-2-IgH* transcript is an optimal target for synthetic oligonucleotides," PNAS USA 94:8150-8155 (1997).

(56) References Cited

OTHER PUBLICATIONS

Nielsen, et al., "Sequence-Selective Recognition of DNA by Strand Displacement with a Thymine-Substituted Polyamide," Science 254:1497-1500 (1991).
Oberhauser, et al., "Effective incorporation of 2'-A-methyl-oligoribonucleotides into liposomes and enhanced cell association through modification with thiocholesterol," Nucl. Acids Res. 20:333-538 (1992).
Petit et al., "Wild-type PINK1 Prevents Basal and Induced Neuronal Apoptosis, a Protective Effect Abrogated by Parkinson Disease-Related Mutations", Journ. Biol. Chem., vol. 280, No. 40, pp. 34025-334032 (2005).
Prasanth, et al., "Regulating Gene Expression through RNA Nuclear Retention," Cell 123, 249-263 (2005).
Prashar & Weissman, "READS: A Method for Display of 3'-End Fragments of Restriction Enzyme-Digested cDNAs for Analysis of Differential Gene Expression," Methods Enzymol., 303:238-272 (1999).
Quantin, et al., "Adenovirus as an expression vector in muscle cells in vivo," PNAS 89:2581-2584 (1992).
Rosenfeld, et al., "In Vivo Transfer of the Human Cystic Fibrosis Transmembrane Conductance Regulator Gene to the Airway Epithelium" Cell, 68:143-153 (1992).
Rosok and Sioud, "Systematic identification of sense-antisense transcripts in mammalian cells," Nature Biotech. 22(1):104-108 (2004).
Saison-Behmoaras, et al., "Short modified antisense oligonucleotides directed against Ha-ras point mutation induce selective cleavage of the mRNA and inhibit T24 cells proliferation," EMBO J. 10:1111-1118 (1991).
Sanghvi, Y.S. in Crooke, S.T, and Lebleu, B., eds., Antisense Research and Applications, CRC Press, Boca Raton, 1993, p. 276-278.
Scheele et al., "The Human PINK1 Locus is Regulated and Vivo by a Non-Coding Natural Antisense RNA During Modulation of Mitochondrial Function", BMC Genomics, vol. 8, No. 1, p. 74 (2007).
Schena, et al., "Parallel human genome analysis: Microarray-based expression monitoring of 1000 genes," PNAS 93:10614-10619(1996).
Shea, et al., "Synthesis, hybridization properties and antiviral activity of lipid-oligodeoxynucleotide conjugates," Nucl. Acids Res 18:3777-3783 (1990).
Shen, T., et al., "Modification of Globin Gene Expression by RNA Targeting Strategies," Experimental Hematology, vol. 35, No. 8, pp. 1209-1218, (2007).
Shimomura, et al., "Semi-synthetic aequorin," J. of Biochemistry (Tokyo) 251:405-410 (1988).
Singer, et al., "Targeting BACE1 with siRNAs ameliorates Alzheimer disease neuropathology in a transgenic model," Nat Neurosci 8:1343-1349 (2005).
Southwick, et al., "Cyanine Dye Labeling Reagents-Carboxymethylindocyanine Succinimidyl Esters," Cytometry 11:418-430 (1990).
Stratford-Perricadet, et al., "Widespread Long-term Gene Transfer to Mouse Skeletal Muscles and Heart," J. Clin. Invest., 90:626-630 (1992).
Sullenger, et al., "Overexpression of TAR sequences Renders Cells Resistant to Human Immunodeficiency Virus Replication," Cell63:601-608 (1990).
Sun, et al., "Downregulation of Sirt1 by antisense oligonucleotides induces apoptosis and enhances radiations sensitization in A549 lung cancer cells," Lung Cancer 58(1):21-29 (2007).
Sutcliffe, et al., "TOGA: An automated parsing technology for analyzing expression of nearly all genes," PNAS, 97:1976-1981 (2000.
Sutton, et al., "TIGR Assembler: A New Tool for Assembling Large Shotgun Sequencing Projects," Genome Science & Tech., 1:9-19 (1995).
Svinarchuk, et al., "Inhibition of HIV proliferation in MT-4 cells by antisense oligonucleotide conjugated to lipophilic groups," Biochimie 75:49-54 (1993).

Tamagno, et al., "The various aggregation states of β-amyloid 1-42 mediate different effects on oxidative stress, neurodegeneration, and BACE-1 expression," Free Radic Biol Med 41:202-212 (2006).
Thakker, D.R., et al., "siRNA-mediated knockdown of the serotonin transporter in the adult mouse brain," Mol Psychiatry 10:782-789 (2005).
Thakker, et al., "Neurochemical and behavioral consequences of widespread gene knockdown in the adult mouse brain by using nonviral RNA interference," PNAS 101:17270-17275 (2004).
Thomas et al., "Intracellular pH Measurements in Ehrlich Ascites Tumor Cells Utilizing Spectroscopic Probes Generated in Situ," Biochemistry 18:2210-2218 (1979).
Thompson, et al., "Synthesis and Applications of Small Molecule Libraries" Chem Rev 96:555-600 (1996).
To, KY, "Identification of Differential Gene Expressionm by High Throughput Analysis," Comb. Chem. High Throughput Screen 3:235-241 (2000).
Tong, et al., "Oxidative stress potentiates BACE1 gene expression," Neural Transm 112, 455-469 (2005).
Toulme, J.J., "New candidates for true antisense," Nature Biotechnology 19:17-18 (2001).
Tsien in Methods in Cell Biology vol. 30 Taylor and Wang (eds.) p. 127-156 (1989).
Ulhman, E., "Recent advances in the medical chemistry of antisense oligonucleotide," Current Opinions in Drug Discovery & Development 3:203-213 (2000).
Van Den Eynde BJ, "T cell defined tumor antigens," Curr Opin Immunol 9:684-693 (1997).
Van Der Bruggen, et al., "Tumor-specific shared antigenic peptides recognized by human T cells," Immunol Rev188:51-64 (2002).
Vanhee-Brossolet and Vaquero, "Do natural antisense transcripts make sense in eukaryotes?" Gene 211:1-9 (1998).
Vaughn, et al., "Human Antibodies with Sub-nanomolar Affinities Isolated from a Large Non-immunized Phage Display Library," Nature Biotechnology, 14:3:309-314 (1996).
Velculescu, et al., "Serial Analysis of Gene Expression," Science 270:484-487 (1995).
Wahlestedt, "Natural antisense and noncoding RNA transcripts as potential drug targets," Drug Discovery Today 11 (11/12):503-508 (2006).
Wahlestedt, C., "Antisense oligonucleotide strategies in neuropharmacology," Trends Pharmacol Sci 15:2:42-46(1994).
Walsh, et al., The role of cell-derived oligomers of Aβ in Alzheimer's disease and avenues for therapeutic intervention, Biochem Soc Trans 33: 1087-1090 (2005).
Wang, B.B, et al., "Identification of a nuclear-specific cyclophilin which interacts with the proteinase inhibitor eglin c," Biochem J. 314 (Pt 1) 313-319 (1996).
Wiesenhofer, et al., "Glial cell line-derived neurotrophic factor (GDNP) is a proliferation factor for rat C6 glioma cells: evidence from ainisense experiments," Antisense & Nucleic Acid Drug Development 10(5):311-321 (2000).
Xue, et al., "Hypoxia and reoxygenation increased BACE1 mRNA and protein levels in human neuroblastoma SH-SY5Y cells," Neurosci Lett 405,231-235 (2006).
Yamada, et al., "Endothelial Nitric-Oxide Synthase Antiserise (NOS3AS) Gene Encodes an Autophagy-Related Protein (APG9-like2) Highly Expressed in Trophoblast" (2005).
Yang, et al., "Cellular and Humoral Immune Responses to Viral Antigens Create Barriers to Lung-Directed Gene Therapy with Recombinant Adenoviruses," J. Virol 69:2004-2015 (1995).
Yoshigai, et al., "Characterization of Natural Antisense Transcripts Expressed from Interleukin 1β-inducible Genes in Rat Hepatocytes," HOAJ Biology; 1-10 (2012).
EP Application No. 06850393.7 Examination Report dated Oct. 18, 2011.
International Search Report and Written Opinion for PCT Application No. PCT/US2010/033078 mailed Jun. 29, 2011.
PCT/US2010/026119 Seareh Report and Written Opinion mailed Feb. 7, 2011.
PCT/US2010/024079 Search Report and Written Opinion mailed Jan. 31, 2011.

(56) References Cited

OTHER PUBLICATIONS

PCT/US2010/027394 Search Report and Written Opinion mailed Nov. 5, 2010.

PCT/US96/10287 (WO97/000271) The Regents of the University of California Jan. 3, 1997.

* cited by examiner

FIG. 2

(SEQ ID NO: 1)

```
>gi|71051575|ref|NM_001025366.1| Homo sapiens vascular endothelial growth
factor A (VEGFA), transcript variant 1, mRNA GGCTTGGGGCAGCCGGGTAGCTCGGAGGTCGTGGCGCTGCGGGCTAGCACCAGCGCTCTGTCGGGAGGCGCAGCG
GTTAGGTGGACCGGTCAGCGGACTCACCGGCCAGGGCGCTCGGTGCTGGAATTTGATATTCATTGATCCGGGTTT
TATCCCTCTTCTTTTTTCTTAAACATTTTTTTTTAAAACTGTATTGTTTCTCGTTTTAATTTATTTTTGCTTGCC
ATTCCCCACTTGAATCGGGCCGACGGCTTGGGGAGATTGCTCTACTTCCCCAAATCACTGTGGATTTTGGAAACC
AGCAGAAAGAGGAAAGAGGTAGCAAGAGCTCCAGAGAGAAGTCGAGGAAGAGACAGAACGGGGTCAGAGAGAGCGC
GCGGGCGTGCCAGCAGCGAAAGCGACAGGGGCAAAGTGAGTGACCTGCTTTTGGGGGTGACCGCCGGAGCGCGGC
GTGAGCCCTCCCCCTTGGGATCCGCAGCTGACCAGTCGCGCTGACGGACAGACAGACAGACACCGCCCCCAGCC
CCAGCTACCACCTCCTCCCGGCCGGCGGCGGACAGTGCACGCGGCGGCCAGCCGCGGGCAGGGGCCGGAGCCCG
CGCCCGGAGGCGGGGTGGAGGGGGTCGGGGCTCGCGGCGTCGCACTGAAACTTTTCGTCCAACTTCTGGGCTGTT
CTCGCTTCGGAGGAGCCGTGGTCCGCGCGGGGAAGCCGAGCCGAGCGGAGCCGCGAGAAGTGCTAGCTCGGGCC
GGGAGGAGCCGCAGCCGGAGGAGGGGGAGGAGCAAGAAGAGAAGGAAGAGGAGAGGGGGCCGCAGTGGCGACTCG
GCGCTCGGAAGCCGGGCTCATGGACGGGTGAGGCGGCGGTGTGCGCAGACAGTGCTCCAGCCGCGCGCGCTCCCC
AGGCCCTGGCCCGGGCCTCGGGCCGGGAGGAAGAGTAGCTCGCCGAGGCGCCGAGGAGAGCGGGCCGCCCCACA
GCCCGAGCCGGAGAGGGAGCGCGAGCCGCGCCGGCCCCGGTCGGGCCTCCGAAACCATGAACTTTCTGCTGTCTT
GGGTGCATTGGAGCCTTGCCTTGCTGCTCTACCTCCACCATGCCAAGTGGTCCCAGGCTGCACCCATGGCAGAAG
GAGGAGGGCAGAATCATCACGAAGTGGTGAAGTTCATGGATGTCTATCAGCGCAGCTACTGCCATCCAATCGAGA
CCCTGGTGGACATCTTCCAGGAGTACCCTGATGAGATCGAGTACATCTTCAAGCCATCCTGTGTGCCCCTGATGC
GATGCGGGGGCTGCTGCAATGACGAGGGCCTGGAGTGTGTGCCCACTGAGGAGTCCAACATCACCATGCAGATTA
TGCGGATCAAACCTCACCAAGGCCAGCACATAGGAGAGATGAGCTTCCTACAGCACAACAAATGTGAATGCAGAC
CAAAGAAAGATAGAGCAAGACAAGAAAAAAAATCAGTTCGAGGAAAGGGAAAGGGGCAAAAACGAAAGCGCAAGA
AATCCCGGTATAAGTCCTGGAGCGTGTACGTTGGTGCCCGCTGCTGTCTAATGCCCTGGAGCCTCCCTGGCCCCC
ATCCCTGTGGGCCTTGCTCAGAGCGGAGAAAGCATTTGTTTGTACAAGATCCGCAGACGTGTAAATGTTCCTGCA
AAAACACAGACTCGCGTTGCAAGGCGAGGCAGCTTGAGTTAAACGAACGTACTTGCAGATGTGACAAGCCGAGGC
GGTGAGCCGGGCAGGAGGAAGGAGCCTCCCTCAGGGTTCGGGAACCAGATCTCTCACCAGGAAAGACTGATACA
GAACGATCGATACAGAAACCACGCTGCCGCCACCACACCATCACCATCGACAGAACAGTCCTTAATCCAGAAACC
TGAAATGAAGGAAGAGGAGACTCTGCGCAGAGCACTTTGGGTCCGAGGGCGAGACTCCGGCGGAAGCATTCCCG
GGCGGGTGACCCAGCACGGTCCCTCTTGGAATTGGATTCGCCATTTTATTTTTCTTGCTGCTAAATCACCGAGCC
CGGAAGATTAGAGAGTTTTATTTCTGGGATTCCTGTAGACACACCCACCCACATACATACATACATTTATATATATA
TATTATATATATATAAAAATAAATATCTCTATTTTATATATATAAATATATATATTCTTTTTTTAAAATTAACAG
TGCTAATGTTATTGGTGTCTTCACTGGATGTATTTGACTGCTGTGGACTTGAGTTGGGAGGGGAATGTTCCCACT
CAGATCCTGACAGGGAAGAGGAGGAGATGAGAGACTCTGGCATGATCTTTTTTTTGTCCCACTTGGTGGGGCCAG
GGTCCTCTCCCCTGCCCAGGAATGTGCAAGGCCAGGGCATGGGGGCAAATATGACCCAGTTTTGGGAACACCGAC
AAACCCAGCCCTGGCGCTGAGCCTCTCTACCCCAGGTCAGACGGACAGAAAGACAGATCACAGGTACAGGGATGA
GGACACCGGCTCTGACCAGGAGTTTGGGGAGCTTCAGGACATTGCTGTGCTTTGGGGATTCCCTCCACATGCTGC
ACGCGCATCTCGCCCCAGGGGCACTGCCTGGAAGATTCAGGAGCCTGGGCGGCCTTCGCTTACTCTCACCTGCT
TCTGAGTTGCCCAGGAGACCACTGGCAGATGTCCCGGCGAAGAGAAGAGACACATTGTTGGAAGAAGCAGCCCAT
GACAGCTCCCCTTCCTGGGACTCGCCCTCATCCTCTTCCTGCTCCCCTTCCTGGGGTGCAGCCTAAAAGGACCTA
TGTCCTCACACCATTGAAACCACTAGTTCTGTCCCCCCAGGAGACCTGGTTGTGTGTGTGAGTGGTTGACCTT
CCTCCATCCCCTGGTCCTTCCCTTCCCTTCCCGAGGCACAGAGAGACAGGGCAGGATCCACGTGCCCATTGTGGA
GGCAGAGAAAGAGAAAGTGTTTTATATACGGTACTTATTTAATATCCCTTTTTAATTAGAAATTAAAACAGTTA
ATTTAATTAAAGAGTAGGGTTTTTTTTCAGTATTCTTGGTAATATTTAATTTCAACTATTTATGAGATGTATCT
TTTGCTCTCTCTTGCTCTCTTATTTGTACCGGTTTTTGTATATAAAATTCATGTTTCCAATCTCTCTCTCCCTGA
TCGGTGACAGTCACTAGCTTATCTTGAACAGATATTTAATTTTGCTAACACTCAGCTCTGCCCTCCCCGATCCCC
TGGCTCCCCAGCACACATTCCTTTGAAATAAGGTTTCAATATACATCTACATACTATATATATTTGGCAACTT
GTATTTGTGTGTATATATATATATATGTTTATGTATATATGTGATTCTGATAAAATAGACATTGCTATTCTGT
TTTTTATATGTAAAAACAAAACAAGAAAAAATAGAGAATTCTACATACTAAATCTCTCTCCTTTTTAATTTTAA
```

FIG. 2 (Continued)

TATTTGTTATCATTTATTTATTGGTGCTACTGTTTATCCGTAATAATTGTGGGGAAAAGATATTAACATCACGTC
TTTGTCTCTAGTGCAGTTTTTCGAGATATTCCGTAGTACATATTTATTTTTAAACAACGACAAAGAAATACAGAT
ATATCTTAAAAAAAAAAAAAGCATTTTGTATTAAAGAATTTAATTCTGATCTCAAAAAAAAAAAAA

SEQ ID NO. 17

>hg18_knownGene_uc003owh.1 range=chr6:43845931-43862201 5'pad=0 3'pad=0
strand=+ repeatMasking=none
GGCTTCGGGCAGCCGGGTAGCTCGGAGGTCGTGGCGCTGGGGGCTAGCACCAGCGCTCTGTCGGGAGGCGCAGCG
GTTAGGTGGACCGGTCAGCGGACTCACCGGCCAGGGCGCTCGGTGCTGGAATTTGATATTCATTGATCCGGGTTT
TATCCCTCTTCTTTTTTCTTAAACATTTTTTTTTAAAACTGTATTGTTTCTCGTTTTAATTTATTTTTGCTTGCC
ATTCCCCACTTGAATCGGGCCGACGGCTTGGGGAGATTGCTCTACTTCCCCAAATCACTGTGGATTTTGGAAACC
AGCAGAAAGAGGAAAGAGGTAGCAAGAGCTCCAGAGAGAAGTCGAGGAAGAGAGAGACGGGGTCAGAGAGAGCGC
GCGGGCGTGCGAGCAGCCGAAAGCCGACAGGGGCAAAGTGAGTGACCTGCTTTTGGGGGTGACCGCCGAGCGCGC
GTGAGCCCTCCCCCTTGGGATCCCGCAGCTGACCAGTCGCGCTGACGGACAGACAGACAGACACCGCCCCCAGCC
CCAGCTACCACCTCCTCCCCGGCCGGCGGCGGACAGTGGACGCGGCGGCGAGCCGCGGGCAGGGGCCGGAGCCCG
CGCCCCGAGGCGGGGTGGAGGGGGTCGGGGCTCGCGGCGTCGCACTGAAACTTTTCGTCCAACTTCTGGGCTGTT
CTCGCTTCGGAGGAGCCGTGGTCCGCGGGGGGAAGCCGAGCCGAGCCGAGAAGTGCTAGCTCGGGCC
GGGAGGACCCGCAGCCGGAGGAGGGGAGGAGGAAGAAGAGAAGGAAGAGGAGAGGGGGCCGCAGTGGCGACTCG
GCGCTCGGAAGCCGGGCTCATGGACGGGTGAGGCGGCGGTGTGCGCAGACAGTGCTCCAGCCGCGCGCGCTCCCC
AGGCCCTGGCCCGGGCCTCGGGCCGGGAGGAAGAGTAGCTCGCCGAGGCGCCGAGGAGAGCGGGCCGCCCCACA
GCCCGAGCCGGAGAGGGAGCGCGACCCGCGCCGGCCCCGGTCGGGCCTCCGAAACCATGAACTTTCTGCTGTCTT
GGGTGCATTGGAGCCTTGCCTTGCTGCTCTACCTCCACCATGCCAAGgtaagcggtcgtgccctgctggcgccgc
gggccgctgcgagcgcctctcccggctgggacgtgcgtgcgagcgcgcgcgtgggggctcgtgcccacgcgg
gtccatgggcaccaggcgtgcgcgtccccctctgtcgtcttaggtgcaggggaggggcgcgcgcgctaggtg
ggagggtaccgggagagaggctcaccgccacgcgggccctgcccaccacggagtcaccgcacgtacgatctg
ggccgaccagccgagggcggagccggaggaggaggccgaggggctgggcttgcgttgcgctgcgggctgaag
tttgctcccgggctggtcccggacgaactggaagtctgacgcgggcgcgggagccagagaccagtgggcag
ggggtgctcggaccttggaccgcgggagggcagagagcgtgagggggcaggcgcaggaggagaggggggcttg
ctgtcactgccactcggtctcttcagccctcgcgcgagtttgggaaaagttttgggtggattgctgcggggac
ccccctcctgctgggcacctgcgccgcgcaacccgccgtccccgctcgcgtcccgctcggtgccagcc
tccccgccccggcgtgcgcgcgcgcgagccgattacatcagccgggcctggccggcggcgcgcgtgttccgg
agcctcggctgcccgaatgggggagcccagagtggcgagccgcaccctccccccgcagccctccgcgggaaggt
gacctctcgaggtagccccagcccgggatccagagaaccatccctaccccttcctactgtctccagaccctacc
tctgccagtgctaggaggaattcctgaccgccctctctcacccatttccttttagcctggagagaagcc
ctgtcacccgcttattttcattctctctgcgggagaagatccatctaaccccttctgtccagagtccaggg
aaaggatgatcactgtcagaagtcgtggcgcgggagccactggggcttgtcacattcaccgaaagtcccga
cttggtgacagtgtgcttccttccctcgccaacagttccgagtgagctgtgctttagctctcgtggggtgggt
caagggaggattgaagagtcattgccccactttttggagaaatggcttgaaattttgctgtgacacggg
cagcatgggaatagtccttcctgaaccctggaaaggagctcctgccagccttgcacacactttgtcctggtgaaa
ggcagcctgagcaggtgttttttggaactccaaacctgcccacccaacttgcttctgaaagggactctaaag
ggtccctttccgctcctctctgacgcttccctcagccagaattccctggagaggaggcaagagggaaagccatg
gacaggggtgctgctaacaccgcaagttcctcagaccctgcaccaaaggccttggctacaaggcctccaagtagg
gaggaagggggaggagtggctgcctggcacagtgtgaccttcagaggccccagagaaggacacctggccctgc
ctgcctagaaccccctcctgtgctccctggccttggaaggggtatgaaatttccgtcccctttcctccttgggt
gcccaggaggagtggagggtccgggagaatattgtcaggggaaggcaggggtgtcatgggaatgggtgaggg
ggctgaggtgcagaatccaggggggtccctgcaggagccgcagtggtaagctgtccagctggaagctggtaactg
ttgtttctcttgagagggcttcctgtgaccttggctgtctgtgggagcagggctgggtacctgagtgggtg
cattggggtgtggaaggagaggaaagaaagatggacagtgggactctctccccctagcagggtctggtgttcc
gtaggctagagtgccctctgctctgcgagtgctgggcgggagggagttggtgagagctggagaccccaggaa
gggctggcagaagccttttcctttggggtgctgtcaggtccgcatgtcttggcgtgttgaccttcacagcttctgg
cgagggaggaatgatctgatgcgggtgggagggttagaggaggcctcaggcctaaggtggtgcagggggccc
ctagggcgtgggcagtgccaaggcataaaagccttcctggtccctggtggcatttgaaggtgcccaggtgagag
gggcttggcacctcctcaccctggggagggagaagaaccaggaacaggtaggagtgggagacaggtgaggctt
ggaaatctattggtgctctggagagatttgtgtagagagaaatggtgttctccccccagggtctcctccttgggt
ttttacccctcaagcaacctgtgggcatgctgggttattcctaaggactagaagagcttggatggggaggtgg
ttggtgccttcggtcctcggcacccctccgtctccaacaccagctcaccctggtatttgtcatgtcagcagg
agaaggtcaccatgcttgttttttctcgccccctagtcctccttcctgccccagtccaaattgtcctcctatttga
ccttaatacttaccatggctttggaccagggaactagggggtatagtgagagcaggagagggaagtgtgggaag
gtacaggggacctcgacgcttgaagcattctgggggttttcctcctgcattcgagctcccagccccaacatctg
gttagtctttaaacttcctcgggttcataacatagcagtccaggagtggtgggcatattctgtgccgtgggac
ccccggttgtgtcctgtctgactcagaagacttgagaagccagaggctgttggtgggaggaagtgaggaggga
ggaggggctaggtggctgggcctgtcaccccagcccctgcccatgcccatgccttgctctctttctgtcctcag
TGGTCCCAGGCTGCACCCATGGCAGAAGGAGGAGGGCAGAATCATCACGAAGgtgagtcccctggctgttggat

FIG. 2 (Continued)

```
ggggttccctgtcctctcaggggatgggtggatggcctaattcctttttcttcagaactgtggggaggaagggga
agggggcacaggaatataaggatcaagaaagaaagagctgggcaccaacgaggttcacccttcagtttcgtgaggact
ctccgctgttcaggtctctgctagaagtaggacttgttgccttttcttctgtctcttccagtaaaattttattt
ggagaaggagtcgtgcgcacagagcaggaagacagtgttcagggatcctaggtgttgggggaagtgtcccttgtt
tcccctagctcccaggggagagtggacatttagtgtcattcctatatagacatgtcccatttgtgggaactgtg
accccttcctgtgtgagctggaggcacagagggctcagcctaatgggatctctcctccttccctggtttgcattc
ctttgggggtggagaaaaccccatttgactatgttcggctgctgtgaacttccctccaggccagcagagggctg
gctgtagctcccaggcgccccgcccctgccaacccgagtccgcctgcttttgttccgttgtggtttggat
cctcccatttctctggggacaccctggctctcccaccactgactgtggcctgtgctctccacctctggggaggg
aaggccctgggtcttccttcccgcgagtttccctgacctaaatctgggctggctgggtagtggccagcagtgt
gatgccagcctgttctgcctcctccttcccaccccaggagcccttcttggcctaggactggcttctcagc
cactgaccggcccctgcttccagtgcgccacttacccccttccagcttcccagtggtctctggtctgggagaggc
aggacaaaggtctttgttgctggagaaaaggttgtctgcgataaataaggaaaaccacgaaagcctggttgttg
gagtgtacgtgtgtgctccccaggcagtggaggccagcccttcctggaggggcggctgcctgatgaaggatgcg
ggtgaggttcccggcctccacctccatgggacttgggattcattccaagggaggagcttttttggggggaattcct
acccccaggtctttttaccctcagttaccaacccttgcccaggcccagacctctgctatcccctcctgggccac
aagcctggcctcctctgtcccaattgtgatgaaggggcagttcaaaacttcttgattagtcatcttctccccta
tcgacttggcttaaaaaatgacctttcagactctagtctcgttcactcttttttgatgatgcttgccgtaac
cctgtgggtagagaaggattctgtgcccattggtggtctggataaaagaaatagagacctcacaggaagcagt
ggactggcctgtttccccactgttcttctgttttcacactgtggccttctcccacctcttcccaatcaacc
tattgtgtacatagccccctcattgtcctttattcttctggaaagcagaccttggagggagggagtgaggggcag
gctcagctgtggtctctgggggtgggggttgggagctgggtggaagtccacgaagcatacacttaagatgctt
tggtgaagttctaaacttcatattaccccaggctgaaaaagagccacttgttcctcagggctggaaatggaagccaa
aacaccaccttttcagcctgtttcagcatcttttagagatcagcccaacccacttacacagttgagcagagttgg
aggcctagagaggggagggactgggcccaaggtcataccaactcatggccagagcctgggcctcctcactggccag
gtgttatttcttccctctgggtagggaacctatttcagggacaggattgctatgtggtagtggtggtggggtgcg
ataggccgtggcaggctgggcacaattggagtagtcatgcatgccagactcctgcatttattattctcaaggggccc
gcctctgtggcccagaattaccccttcatgctccagtgcaccccaggcttcgtggccagcctgggaaactgtctc
taccctggtctcccttcagatcagcttctagaaatgtttcgtggctacagtggcagcactgttttttccatgatg
caagcagtttgccctcttgggcgggttatcagtggctggcagggctggcacagcgtgtccgcccactgccacct
gtgggttccaggaggccagccccctgtctgctgatgccacacctctcagctcatctcatgctggggaagaggactgg
caggggggaaaggtgcctcctcctgaaaggtgcctcctctgttttttgcctaatatagcttgggaacactttgatg
tcagctaattctgactcctttacttactagctgtgcggccttggggcaacttacttagcctcttgagcctcctg
ttccccatctgtaaaatggaatctcaatagtgtctaatagtaccatgtggagaaacttgtgtgaaatgatagctg
tggactactgtacacagtactcaggatgtagtaagtgctcaataaacagctgttggtatgttgacgttatgta
gtggttgtgggggaggactaggaaactggagactagcttggcaaagctggctcttcctccttttagggaaagctt
agagcatccccatgggtatacccatactcagactgtctctctggcatcgaggttggcccaggattcagttcagct
gtcacagtgaggtggcgggatcagatgtggcaggccatgtccttggaacttgagtacatcgtgtgatctctgga
atgaaaacaggccttcaccagtgtttgatcggtggaaaggaagtgcttcaaaacacagtaggagggagcttac
gttagattttgaaggactttgcctgattcggaagctccaaagagtggcattacagctgggtggagagaggggc
tagccatctttgtgtcgccaccgggctcatgtgtcatcgcctctcatgcagTGGTGAAGTTCATCGATGTCTA
TCAGCGCAGCTACTGCCATCCAATCGAGACCCTGGTGGACATCTTCCAGGAGTACCCTGATGAGATCGAGTACAT
CTTCAAGCCATCCTGTCTGCCCCTCGATGCCGATCCGGGCCTCCAATGACGAGACCAGGGCCTGAGTGTGTGCCCAC
TGAGGAGTCCAACATCACCATGCAGgtgggcatctttgggaagtggggcaaggggggataggggagggggcaac
actttggggaacaggtggtccccaggtcgttcctggctagatttgccttgtctggctcctgccctgagttgcaca
ggggaggtatgtggggtcttgccttctgtgagaagatgcttcattccagccaggttcccagcaagccccaa
ccatctccttccctgatggttgccatgggcctcaggaggggacaggtggatggctcctgtgtcaggagccccctc
tcccctcttggagagagtcctgagtgccccccttcttgggggcttttgtttgggaagctggatgagcctgtcc
atggagagtttaaaaagtctttttggtgttacctggtaatgggcacatctcagcccagatagggtgggagggagc
tgtgaaacaagggagggggttgcttcgggtatctactaggagtcagggtgaagcctagagaggatgaaagaag
gggaggggatgggagtggtaagaacctaggatttgaattccgggctggccaacctgtgtcttggc
ctcaagtggaacaaggctccttgaggccagcagggttggggggagttgggtgggcctgagcctcttttcctgcta
gagctcttggtcctccctcaccaccaatccgtgtctgcagaaccctgggtgctgagtgcaggagccc
cagggttgtcccatctgggtatggctggctgggtcactaacctctgtgatctgcttccttccttccagATTATG
CGGATCAAACCTCACCAAGGCCAGCACATAGGAGAGATGAGCTTCCTACAGCACAACAAATGTGAATGCAGgtga
ggatgtagtcacggatcattatcagcaagtggctgcaggctgctgatctgtgccaggttaagcatgctgtac
ttttggccccgtccagtcccgctatgtgacctggcattttacttcaatgtgcctcagtttctacatctg
taaaatgggcacaatagtagtatacttcatagcattgttataatgattaaacaagttatatatgaaagattaaa
acagtgttgctccataataaatgctgttttactgtgattatttattgttgttatccctatcattatcatcaccat
cttaaccctcctgttttgctcttttctctctcctacccattgcagACCAAAGAAAGATAGAGCAAGACAAGA
AAAgtaagtggccctgactttagcacttctcctctccatggccgctgtcttggtttggggctcttggctacct
ctgttggggggctccatagcctcctgggtcaggactggtcttgtggggactttgtggtggcagcaacaatgg
gatggagccaactccaggatgatggctctaggctagtgagaaaacatagccaggagcctggcacttcctttgga
agggacaatgcctctgggtctccagatcattcctgaccaggacttgctgtttcggtgtgtcaggggcactgtg
gacactggctcactggcttgtctaggacaccacgtggagagggagtggcagagagccagcttttg
tgtgtcagaggaaatggctcttttgctgctgctgtgacggtgcagttggatgcgagggccggtggagggtggt
ttctaagtgcatgccctcctgtaggcgcaggcggcagacacagccctcttggccaggagaaaagttgaat
gttggtcattttcagaggcttgtgagtgctccgtgttaaggggcaggtaggatgggtggggacaaggtctggc
ggcagtaaccccttcaagacagggtgggcggctggcatcagcaagagcttgcagggaaagagagactgagagagag
```

FIG. 2 (Continued)

```
cacctgtgcctgcccttttccccacaccatcttgtctgcctccagtgctgtgcggacattgaagcccaccag
gcctcaaccccttgctcttccctcagctcccagcttccagagcgaggggatgcggaaaccttccttccaccctt
tggtgctttctcctaaggggggacagacttgccctctctggtccttctccccctccttttcttcctgtgacagac
atcctgaggtgtgttctcttgggcttggcaggcatggagctctggttctcttgaaggggacaggctacagcct
gcccccctcctgttctcccaaatgactgctctgccatgggagagtaggggctcgctgggctcggaagagtg
tctggtgagatggtgtagcaggctttgacaggctggggagagaactccctgccaagtaccgccaagctctcct
cccagacctccttaactcccaccccatcctgctgcctgcccagggctccaggacaccagcctgcctcccagt
ccaggtcgtgctgagcaggctggtgttgctcttggttccgtgccagctcccaaggtagccgcttcccccacacg
ggattcccagaggttctgtcgcagttgcaaatgaaggcacaaggcctgatacacagccctccctccactcctgc
tccccatccaggcaggtctctgaccttctcccaaagtctggcctaccttttatcacccccggaccttcagggtc
agacttggacagggctgctgggcaaagagccttccctcaggctttgccccctgccggggactgggagccactgtg
agtgtggagaccttttcgggtcctgtgccctccaccagtctccggctccaccaaagccttgtcaggggctgggtt
tgccatcccatggtgggcagcgtgaggagaagaagagccatcgagtgcttgctgccccagacacgctgtgtgcg
cccgcgcatgcctcccagagaccacctgcctcctgacacttcctccgggaagcggccctgtgtggctttgcttt
ggtcgttcccccatccctgcccaccttaccacttcttttactccccccaccgccccgctctctctctgtctctg
ttttttattttccagAAAATCAGTTCGAGGAAAGCGAAAGCGGGCAAAAACGAAAGCGCAAGAAATCCCGGTATA
AGTCCTGGAGCGTGTACGTTGGTGCCCGCTGCTGTCTAATGCCCTGGAGCCTCCCTGGCCCCCAgtacaacctcc
gctgccattcctgtaacctgcctccctccccctggtccttcctggctctcatcctcctggccgtgtctctc
tctcactctctcactccactaattggcaccaacgggtagatttggtggtggcattgctggtccagggttgggtg
aatgggggtgccgacttggcctggaggattaagggaggggaccctggcttggctgggcaccgattttctctcacc
cactggcactggtgcggggccatgttggcacaggtgctgctcaccaactggtttccattgctctaggcttc
tgcactctgtctggaagctgagggtgtggggagggcagacatggcccaagaagggctgtgaatgactggagcag
cttgctgaatgactccttggctgaaggaggagcttgggtgggatcagacaccatgtggcggcctccttcatctg
gtggaagtgccctggctcctcacggaggtggggcctctggaggggagcccctattccggcccaaccatggcac
ccacagaggctccttgcaggcagctcttcctcgtggtcggaggctggtgggccctgccctgggccctctg
gccaccagcggcctggcctggggacaccgcctccgggcttagcctcccatcacacctactttagcccacccttgg
tggaagggctggacatgagccttgcacggggagaagtggcccctgattgccatcccagcaggtgaagagtca
aggcgtgctccgatgggggcaacagcagttgggtccctgtggcctgagactcaccttgtctcccagagacacag
cattgccccttatggcagcctctccctgcactctctgccgtctgtgccgcctctcctgcggcaggtgtccta
gccagtgctgcctctttccgccgctctctgtctttgctgtagcgctcggatccttccagggccggggggctg
accggctgggtggggtgcagctgcggacatgttaggggtgttgcatggtgatttttttctctctctctgctg
atgctctagcttagatgtcttttccttttgcttttttgcagTCCCTGTGGGCCTTGCTCAGAGCGGAGAAAGCATT
TGTTTGTACAAGATCCGCAGACGTGTAAATGTTCCTGCAAAAACACAGACTCGCGTTGCAAGGCGAGGCAGCTTG
AGTTAAACGAACGTACTTGCAGgttggttccagagggcaagcaagtcagagggggcatcacacagagatgggg
agagagagagagaaagagagtgagcgagcgagcgagcgggagagcgcctgagaggggccagctgcttgctcagtt
tctagctgcctgctggtgactgctgccttctctgcttttaaggccctgtggtgggctgcaggcactggtccag
cctggcggggcctgttccgaggttgccctggttgcctgagtggtaggctggtgtggcttagtgtagtggtgtgga
cgcaagctgtgtgttgtcctgctgtggtcctctgctcataagtggctgtttgctcctgatgttattaccacctctgg
tagtaatgctgagaagctgaaagccgattccaggtgtggacaatgtcaacaaagcacagatgctctcgctgggc
cttgcctcggcctttgaagtctgcatggctgggcttctcactcactcagtgtttcttgctggggaaggaattg
agtctcccacttcagactgggcctccctgaggaaagggttgtgtctcccactcagactgaggttccctgagcgt
agggctgtgtctctccctccgactgggctccctgataggggctgctcccgctcagactgaggctgaggtccctcagg
ccaggctatgtctccctcctcagactggggtctgagggcaaggggtctgcgctgttcgtttaggatgggggcact
tttgcctacacactgaaggagctgtagccatccaagaatactagatacctttaatcctccaccagtcatggtgaca
accccaagcagcccacacattttcaagtgccccaggatgcgtggagggagggtctgtgcccattctcctgaca
ttagcctgtgagctccgtaagccggctcctgtttacctcttgtgagccccgggcatctgtacctcttcct
ttgcccatactgggaccaaggaagtgtcaagtgcatgagtgaatgtgtgactcagttcagagggtgaggtcagg
agcacagggtcgggacaggtggctggcatcttaatgccttagcttatgttcttttataccaacttggcctgtgc
tcagagtgagggaggccctgggggtcagggtaagcgtcagtcagggaggcaagacttttgtggggattttctagac
agggccaaggcacccccagctcaccccgaggctgtgttagggaagtccttggagtcgtctcccctccccagcaat
gttcttgtcgcttgtctgtcaggggatgctggggacaggcctggtagttggtgggctgctgtctgtct
tggccctatgtgaaaccaagagggcgtatattagtgctggggtggggctctgcctaacttcaggctggatgag
gggagtctcagttccccaggggtcctgggaaagataagggacttgacattttaggttttaggtgattattct
gctgatgggtttgtgtgaagtgacctgggagctaactgaagttactctaacctcccaataccttaccccaacc
ccaagctgctgtatctggaatatcagtttccaaaattggagcttaggactccgtttcggggctcccagaa
gggtaggccctgttctgctcctctcacaatcaccccggcaggcatgctgagaaagttcttggaggccc
ctttgcttcagctggagtagtgaagccgcgaattgtctctcccatcctaagtgaagcagcatattgaaagga
aagacaacctgttacctggcctgcaacctccaggcagctcaagagagatgaggcctacagccacagtgggaggg
gacatggagcagatggcctcctcacctggccctcctgctctacgctaccccctgggagcctcctgt
cccagggcaggccttgccattgttggtcacccggccaagctctctgcctcaggcggttctcccagaagatctg
cccactctcttcccacaccagccctagagactgaactgaaaaccctcctcagcagggagcctcttctgattaa
cttcatccagctctggtcacccatcagctcttaaaatgtcaagtggggactgttctttggtatccgttcatttgt
tgctttgtaaagtgttccatgtccttgtcttgtctcaagtagattgcaagctcaggggttagactgggagcc
ctgagtggagctgctgctcaggcggggctccttgagggcaggggctgttctcatactggggctttctgc
cccaggaccacaacttcctgtcctctctgtctttatggtccggaggctgcagtgaccagggggcccaggaat
ggggaggccgcctgctcatgccaggcctcctcacttggccctaaccccagccttttgttttccatttccctcag
ATGTGACAAGCCGAGGCCGGTGAGCCGGCCAGGACGGAAGGAGCCCTCCCTCAGGGTTTCGGGAACCAGATCTCTCAC
CAGGAAAGACTGATACAGAACGATCGATACAGAAACCACGCTGCCGGCCACCACACCATCACCATCGACAGAACAG
TCCTTAATCCAGAAACCTGAAATGAAGGAAGAGGAGACTCTGCGCAGAGCACTTTGGGTCCGGAGGGCGAGACTC
```

FIG. 2 (Continued)

```
CGGCGGAAGCATTCCCGGGCGGGTGACCCAGCACGGTCCCTCTTGGAATTGGATTCGCCATTTTATTTTTCTTGC
TGCTAAATCACCGAGCCCGGAAGATTAGAGAGTTTATTTCTGGGATTCCTGTAGACACACCCACCCACATACAT
ACATTTATATATATATATATATTATATATATATAAAAATAAATATCTCTATTTTATATATATAAAACATATATATTC
TTTTTTTAAATTAACAGTGCTAATGTTATTGGTGTCTTCACTGGATGTATTTGACTGCTGTGGACTTGAGTTGGG
AGGGGAATGTTCCCACTCAGATCCTGACAGGGAAGAGGAGGAGATGAGAGACTCTGGCATGATCTTTTTTTTGTC
CCACTTGGTGGGGCCAGGGTCCTCTCCCCTGCCCAGGAATGTGCAAGGCCAGGGCATGGGGGCAAATATGACCCA
GTTTTGGGAACACCGACAAACCCAGCCCTGGCGCTGAGCCTCTCTACCCCAGGTCAGACGGACAGAAAGACAGAT
CACAGGTACAGGGATGAGGACACCGGCTCTGACCAGGAGTTTGGGGAGCTTCAGGACATTGCTGTGCTTTGGGGA
TTCCCTCCACATGCTGCACGCGCATCTCGCCCCCAGGGGCACTGCCTGGAAGATTCAGGAGCCTGGGCGGCCTTC
GCTTACTCTCACCTGCTTCTGAGTTGCCCAGGAGACCACTGGCAGATGTCCCGGCGAAGAGAAGAGACACATTGT
TGGAAGAAGCAGCCCATGACAGCTCCCCTTCCTGGGACTCGCCCTCATCCTCTTCCTGCTCCCCTTCCTGGGGTG
CAGCCTAAAAGGACCTATGTCCTCACACCATTGAAACCACTAGTTCTGTCCCCCCAGGAGACCTGGTTGTGTGTG
TGTGAGTGGTTGACCTTCCTCCATCCCCTGGTCCTTCCCTTCCCTTCCCGAGGCACAGAGAGACAGGGCAGGATC
CACGTGCCCATTGTGGAGGCAGAGAAAAGAGAAAGTGTTTATATACGGTACTTATTTAATATCCCTTTTTAATT
AGAAATTAAAACAGTTAATTTAATTAAAGAGTAGGGTTTTTTTTCAGTATTCTTGGTTAATATTTAATTTCAACT
ATTTATGAGATXTATCTTTTGCTCTCTCTTGCTCTCTTATTTGTACCGGTTTTTGTATATAAAATTCATGTTTCC
AATCTCTCTCTCCCTGATCGGTGACAGTCACTAGCTTATCTTGAACAGATATTTAATTTTGCTAACACTCAGCTC
TGCCCTCCCCGATCCCCTGGCTCCCCAGCACACATTCCTTTGAAATAAGGTTTCAATATACATCTACATACTATA
TATATATTTGGCAACTTGTATTGTGTGTATATATATATATATATGTTTATGTATATATGTGATTCTGATAAAAT
AGACATTGCTATTCTGTTTTTTATATGTAAAAACAAAACAAGAAAAAATAGAGAATTCTACATACTAAATCTCTC
TCCTTTTTAATTTTAATATTTGTTATCATTTATTTATTGGTGCTACTGTTTATCCGTAATAATTGTGGGGAAAA
GATATTAACATCACGTCTTTGTCTCTAGTGCAGTTTTTCGAGATATTCCGTAGTACATATTTATTTTTAAACAAC
GACAAAGAAATACAGATATATCTTAAAAAAAAAAAAGCATTTTGTATTAAAGAATTTAATTCTGATCTCAA
```

FIG. 3

Natural antisense sequence (vegfaas): SEQ ID NO: 2

>gi|14452617|gb|BI045995.1|BI045995 MR3-FN0206-020201-006-a08 FN0206 Homo sapiens cDNA, mRNA sequence GAACGTGGTGATGCGGTGCTTGGGAGCTGGCACGGAACCAAGAGCAACACCAGCCTGCTCAGCACGACCTGGACT
GGGAGGCAGGCTGGGTGTCCTGGAGCCCTGGGCAGGCAGCAGGATGGGGTGGGAGTTAAGGAGGTCTGGGGAGGA
GAGGCTTGGGCGGTACTTGGCAGGGAGTTCTCTCCCCAGCCTGTCAAAGCCTGCTACACCATCTCACCAGACACT
CTTCCGAGCCCAGGCGAGCCCCTACTCTCCCCATGGCAGAGCAGTCATTTGGGGAAACAGGAAGGGGGCAGGC
TGTAGCCTGTCCCCTTCAAGAGAACCAGAGCTCTCCATGCCTGCCAAGCCCAAGAGAACACACCTCAGGATGTCT
GTCACAGGGAAGAAGGAGGGGGAGAAGGGGCCAGAGAGGGCAAGTCTGTCCCCCTTAGGAGAAAGCACCAAAGG
GTGGAAGGAAGGTTTCCGCATCCCCTCGCTCTGGAAGCTGGGAGCTGAGGGAAGAGGCAAGGGGTTGAGGCCTGG
TGGGGCTTCAATGTCCGCACAGCCGTGGACGCAGACAAGATGGTGTGCGGGAAAGGGCAGGGCACAGGTGCTCT
CTCTCAGTCTCTCTTTCCCTGGAAGCTCTTGGTGATGCAAACG Natural antisense sequence (VEGRas): SEQ ID NO: 3

>gi|12175703|gb|BF829784.1|BF829784 MR3-HN0062-221200-009-a05 HN0062 Homo sapiens cDNA, mRNA sequence ANTGGAGACAGGCTGGGATCAGCACTGCTGGCACTACCCAGCCACGCCAGATTTAGGTCAGGGAAACTCGCTGGG
AAGGAAGACCCCAGGGTCTTCCCTCCCCAGAGGTGGAGAGCACAGGCCACAGTCAGTGGTGGGGAGAGCCAGTGT
GTCCCCAGAGAACTGGGAGGATCCAAACCACAACGGAACAAAAGGCAGGCGGACTCGGGGTTGGGCCGCGGGGCG
GATAGCCTGGGAGCTACAGCCAGCCCTCTGCTGGCCGTGGGAGGGACAGTCACAGCAAGCGAACATAGTCAAGTG
GGGTTATCTCCACCCCCAAAGGAATGCAAACCAGGAAAGGGAGGGGAGATCCCATTAGGCTGAGCCCTCTTCCCC
AGCCCAGGCTTGGGGAACAGGGGCGATGGTAGGGGCAAGTGGTTTCTGGGTCCCTAGCCCTGCGTGAAACGGGTT
CCAGACCAAAGAGCCCTGATGAAGGCATGTCTCTATATACTCTATCCCTCTTCCCCAGCCCAG

FIG. 4

| Sequence ID | Sequence |
|---|---|
| SEQ ID NO: 4 | CTGAGCAGGCTGGTGTTGCTCTTGGTT |
| SEQ ID NO: 5 | ACAGACATCCTGAGGTGTGTTCTCTTG |
| SEQ ID NO: 6 | GTTTGCATCACCAAGAGCTTCCAGGGA |

FIG. 5

| Sequence ID | Sequence |
|---|---|
| SEQ ID NO: 7 | CAGCAGTGCTGATCCCAGCCTGTCTCC |
| SEQ ID NO: 8 | GTATATAGAGACATGCCTTCATCAGGG |
| SEQ ID NO: 9 | GGCTGGCTGTAGCTCCCAGGCTATCCG |

FIG. 6

| Sequence ID | Sequence |
|---|---|
| SEQ ID NO: 10 | ATGCCAAGTGGTCCCAGGCTGCACC |
| SEQ ID NO: 11 | GTAGCCTGTCCCCTTCAAGAG |
| SEQ ID NO: 12 | GCGGATAGCCTGGGAGCTA |
| SEQ ID NO: 13 | CAGACATCCTGAGGTGTGTTCT |
| SEQ ID NO: 14 | TGTTCGGTTGCTGTGACTGT |
| SEQ ID NO: 15 | ATGCCTGCCAAGCCCA |
| SEQ ID NO: 16 | CAGCCAGCCCTCTGC |

TREATMENT OF VASCULAR ENDOTHELIAL GROWTH FACTOR (VEGF) RELATED DISEASES BY INHIBITION OF NATURAL ANTISENSE TRANSCRIPT TO VEGF

CROSS REFERENCE

This application is a divisional of U.S application Ser. No. 13/132,997 filed Jun. 15, 2011, now U.S. Pat. No. 8,927,511, which is a National Phase application of PCT/US2009/066455 filed on Dec. 2, 2009, which is based upon U.S. Provisional No. 61/119,957 filed on Dec. 4, 2008, which are all hereby incorporated by reference.

FIELD OF THE INVENTION

Embodiments of the invention comprise oligonucleotides modulating expression and/or function of VEGF and associated molecules.

BACKGROUND

DNA-RNA and RNA-RNA hybridization are important to many aspects of nucleic acid function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H, an activity that is present in most cell types. Antisense molecules can be delivered into cells, as is the case for oligodeoxynucleotides (ODNs), or they can be expressed from endogenous genes as RNA molecules. The FDA recently approved an antisense drug, VITRAVENE™ (for treatment of cytomegalovirus retinitis), reflecting that antisense has therapeutic utility.

SUMMARY

This Summary is provided to present a summary of the invention to briefly indicate the nature and substance of the invention. It is submitted with the understanding that it will not be used to interpret or limit the scope or meaning of the claims.

In one embodiment, the invention provides methods for inhibiting the action of a natural antisense transcript by using antisense oligonucleotide(s) targeted to any region of the natural antisense transcript resulting in up-regulation of the corresponding sense gene. It is also contemplated herein that inhibition of the natural antisense transcript can be achieved by siRNA, ribozymes and small molecules, which are considered to be within the scope of the present invention.

One embodiment provides a method of modulating function and/or expression of an VEGF polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of a polynucleotide comprising 5 to 30 consecutive nucleotides within nucleotides 1 to 643 of SEQ ID NO: 2 or nucleotides 1 to 513 of SEQ ID NO: 3 (FIG. 3) thereby modulating function and/or expression of the VEGF polynucleotide in patient cells or tissues in vivo or in vitro.

In another preferred embodiment, an oligonucleotide targets a natural antisense sequence of VEGF polynucleotides, for example, nucleotides set forth in SEQ ID NOS: 2 and 3, and any variants, alleles, homologs, mutants, derivatives, fragments and complementary sequences thereto. Examples of antisense oligonucleotides are set forth as SEQ ID NOS: 4 to 9 (FIG. 4).

Another embodiment provides a method of modulating function and/or expression of an VEGF polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of the an antisense of the VEGF polynucleotide; thereby modulating function and/or expression of the VEGF polynucleotide in patient cells or tissues in vivo or in vitro.

Another embodiment provides a method of modulating function and/or expression of an VEGF polynucleotide in patient cells or tissues in vivo or in vitro comprising contacting said cells or tissues with an antisense oligonucleotide 5 to 30 nucleotides in length wherein said oligonucleotide has at least 50% sequence identity to an antisense oligonucleotide to an VEGF antisense polynucleotide; thereby modulating function and/or expression of the VEGF polynucleotide in patient cells or tissues in vivo or in vitro.

In a preferred embodiment, a composition comprises one or more antisense oligonucleotides which bind to sense and/or antisense VEGF polynucleotides.

In another preferred embodiment, the oligonucleotides comprise one or more modified or substituted nucleotides.

In another preferred embodiment, the oligonucleotides comprise one or more modified bonds.

In yet another embodiment, the modified nucleotides comprise modified bases comprising phosphorothioate, methylphosphonate, peptide nucleic acids, 2'-O-methyl, fluoro- or carbon, methylene or other locked nucleic acid (LNA) molecules. Preferably, the modified nucleotides are locked nucleic acid molecules, including α-L-LNA.

In another preferred embodiment, the oligonucleotides are administered to a patient subcutaneously, intramuscularly, intravenously or intraperitoneally.

In another preferred embodiment, the oligonucleotides are administered in a pharmaceutical composition. A treatment regimen comprises administering the antisense compounds at least once to patient; however, this treatment can be modified to include multiple doses over a period of time. The treatment can be combined with one or more other types of therapies.

In another preferred embodiment, the oligonucleotides are encapsulated in a liposome or attached to a carrier molecule (e.g. cholesterol, TAT peptide).

Other aspects are described infra.

BRIEF DESCRIPTION OF THE DRAWINGS

FIGS. 1A and 1B: is a graph of real time PCR results showing the fold change+standard deviation in VEGF mRNA after treatment of HepG2 cells with siRNA oligonucleotides introduced using Lipofectamine 2000, as compared to control. Real time PCR results show that the levels of the VEGFA mRNA in HepG2 cells are significantly increased 48 h after treatment with one of the siRNAs designed to vegfaas (vefaas1_2, P=0.05), and possibly with the second, vefaas1_3 (P=0.1, FIG. 1A). In the same samples the levels of vegfaas RNA were significantly decreased after treatment with either vefaas1_2 or vefaas1_3, but unchanged after treatment with vefaas1_5, which also had no effect on the VEGFA mRNA levels (FIG. 1B). Bars denoted in as vefaas1_2, vefaas1_3, vefaas1_5 correspond to samples treated with SEQ ID NOS 4, 5, and 6 respectively.

FIG. 1C is a graph of real time PCR results showing the fold change+standard deviation in VEGF mRNA after treatment of HepG2 cells with siRNA oligonucleotides introduced using Lipofectamine 2000, as compared to control. Real time PCR results show that the levels of the VEGFA mRNA in HepG2 cells are significantly increased 48 h after treatment with two of the siRNAs designed to vegRas (vegRas1_2, P=0.02 and vegRas1_3, P=0.06,). The results for the change in vegRas RNA levels are pending. Bars denoted as vegRas1_2, vegRas1_3, vegRas1_5 correspond to samples treated with SEQ ID NOS 7, 8, and 9 respectively.

FIG. 2 shows SEQ ID NO: 1: Homo sapiens Vascular Endothelial Growth Factor (VEGF), transcript variant 1, mRNA. (NCBI Accession No: NM_001025366.1) and SEQ ID NO: 17 shows the genomic sequence of VEGF (exons are shown in capital letters, introns in small).

FIG. 3 shows
SEQ ID NO: 2: VEGF Natural antisense sequence (NCBI Accession No.: BI045995)
SEQ ID NO: 3: VEGR Natural antisense sequence (NCBI Accession No.: BF829784)

FIG. 4 shows the antisense oligonucleotides, SEQ ID NOs: 4 to 6 designed to VEGF Natural antisense sequence FIG. 5 shows the antisense oligonucleotides, SEQ ID NOs: 7 to 9 designed to VEGR Natural antisense sequence FIG. 6 shows the target sequence VEGFA exon 1 (SEQ ID NO: 10); Forward primer sequences (SEQ ID NOS: 11 and 12), reverse primer sequences (SEQ ID NOS: 13 and 14) and the reporter sequences (SEQ ID NOS: 15 and 16) of the Custom assays designed by Applied Biosystems Taqman Gene Expression Assay (Hs00173626_m1).

DETAILED DESCRIPTION

Figure 1A:
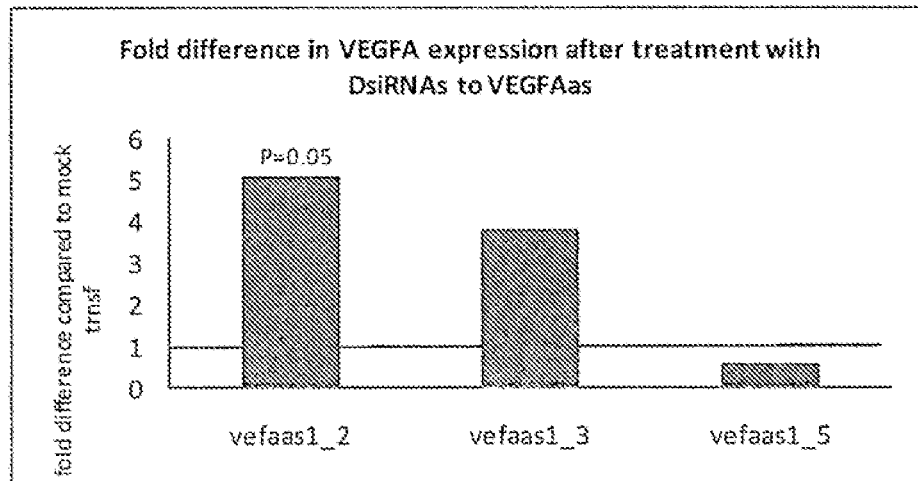
FIGS. 1A, 1B, and 1C.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "mRNA" means the presently known mRNA transcript(s) of a targeted gene, and any further transcripts which may be elucidated.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA (Eguchi et al., (1991) *Ann. Rev. Biochem.* 60, 631-652). An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

In the context of this invention, the term "oligonucleotide" refers to an oligomer or polymer of ribonucleic acid (RNA) or deoxyribonucleic acid (DNA) or mimetics thereof. The term "oligonucleotide", also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoögsteen or reverse Hoögsteen types of base pairing, or the like.

The oligonucleotide may be "chimeric", that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide in the case of an oligonucleotides compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleosides and/or oligonucleotide analogs as described above.

The oligonucleotide can be composed of regions that can be linked in "register", that is, when the monomers are linked consecutively, as in native DNA, or linked via spacers. The spacers are intended to constitute a covalent "bridge" between the regions and have in preferred cases a length not exceeding about 100 carbon atoms. The spacers may carry different functionalities, for example, having positive or negative charge, carry special nucleic acid binding properties (intercalators, groove binders, toxins, fluorophors etc.), being lipophilic, inducing special secondary structures like, for example, alanine containing peptides that induce alpha-helices.

As used herein "VEGF" and "Vascular Endothelial Growth Factor A" are inclusive of all family members, mutants, alleles, fragments, species, coding and noncoding sequences, sense and antisense polynucleotide strands, etc.

As used herein, the words Vascular Endothelial Growth Factor A, VEGF, VEGFA are used interchangeably in the present application.

As used herein, the term "oligonucleotide specific for" or "oligonucleotide which targets" refers to an oligonucleotide having a sequence (i) capable of forming a stable complex with a portion of the targeted gene, or (ii) capable of forming a stable duplex with a portion of a mRNA transcript of the targeted gene. Stability of the complexes and duplexes can be determined by theoretical calculations and/or in vitro assays. Exemplary assays for determining stability of hybridization complexes and duplexes are described in the Examples below.

As used herein, the term "target nucleic acid" encompasses DNA, RNA (comprising premRNA and mRNA) transcribed from such DNA, and also cDNA derived from such RNA, coding, noncoding sequences, sense or antisense polynucleotides. The specific hybridization of an oligomeric compound with its target nucleic acid interferes with the normal function of the nucleic acid. This modulation of function of a target nucleic acid by compounds, which specifically hybridize to it, is generally referred to as "antisense". The functions of DNA to be interfered include, for example, replication and transcription. The functions of RNA to be interfered, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

RNA interference "RNAi" is mediated by double stranded RNA (dsRNA) molecules that have sequence-specific homology to their "target" nucleic acid sequences (Caplen, N. J., et al. (2001) *Proc. Natl. Acad. Sci.* USA 98:9742-9747). In certain embodiments of the present invention, the mediators are 5-25 nucleotide "small interfering" RNA duplexes (siRNAs). The siRNAs are derived from the processing of dsRNA by an RNase enzyme known as Dicer (Bernstein, E., et al. (2001) *Nature* 409:363-366). siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion (Bernstein, E., et al. (2001) *Nature* 409:363-366; Boutla, A., et al. (2001) *Curr. Biol.* 11:1776-1780). Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non limiting embodiments, siRNAs can comprise about 5 to about 40 nt, about 5 to about 30 nt, about 10 to about 30 nt, about 15 to about 25 nt, or about 20-25 nucleotides.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

By "enzymatic RNA" is meant an RNA molecule with enzymatic activity (Cech, (1988) *J. American. Med. Assoc.* 260, 3030-3035). Enzymatic nucleic acids (ribozymes) act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through base pairing, and once bound to the correct site, acts enzymatically to cut the target RNA.

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA (Sullenger et al. (1990) *Cell,* 63, 601-608). This is meant to be a specific example. Those in the art will recognize that this is but one example, and other embodiments can be readily generated using techniques generally known in the art.

As used herein, the term "monomers" typically indicates monomers linked by phosphodiester bonds or analogs thereof to form oligonucleotides ranging in size from a few monomeric units, e.g., from about 3-4, to about several hundreds of monomeric units. Analogs of phosphodiester linkages include: phosphorothioate, phosphorodithioate, methylphosphornates, phosphoroselenoate, phosphoramidate, and the like, as more fully described below.

The term "nucleotide" covers naturally occurring nucleotides as well as nonnaturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytostine, 2-hydroxy-5-methyl-4-triazolopyridin, isocytosine, isoguanin, inosine and the "non-naturally occurring" nucleotides described in Benner et al., U.S. Pat. No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and 2'-hydroxyl sugars, e.g., as described in Kornberg and Baker, DNA Replication, 2nd Ed. (Freeman, San Francisco, 1992) as well as their analogs.

"Analogs" in reference to nucleotides includes synthetic nucleotides having modified base moieties and/or modified sugar moieties (see e.g., described generally by Scheit, Nucleotide Analogs, John Wiley, New York, 1980; Freier & Altmann, (1997) Nucl. Acid. Res., 25(22), 4429-4443, Toulmé, J. J., (2001) Nature Biotechnology 19:17-18; Manoharan M., (1999) Biochemica et Biophysica Acta 1489:117-139; Freier S. M., (1997) Nucleic Acid Research, 25:4429-4443, Uhlman, E., (2000) Drug Discovery & Development, 3: 203-213, Herdewin P., (2000) Antisense & Nucleic Acid Drug Dev., 10:297-310); 2'-O, 3'-C-linked [3.2.0] bicycloarabinonucleosides (see e.g. N. K Christiensen., et al, (1998) J. Am. Chem. Soc., 120: 5458-5463; Prakash T P, Bhat B. (2007) Curr Top Med Chem. 7(7):641-9; Cho E J, et al. (2009) Annual Review of Analytical Chemistry, 2, 241-264). Such analogs include synthetic nucleotides designed to enhance binding properties, e.g., duplex or triplex stability, specificity, or the like.

As used herein, "hybridization" means the pairing of substantially complementary strands of oligomeric compounds. One mechanism of pairing involves hydrogen bonding, which may be Watson-Crick, Hoögsteen or reversed Hoögsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. In general, stringent hybridization conditions comprise low concentrations (<0.15M) of salts with inorganic cations such as $Na^{++}$ or $K^{++}$ (i.e., low ionic strength), temperature higher than 20° C.-25° C. below the Tm of the oligomeric compound:target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1× sodium chloride-sodium citrate buffer (SSC)/0.1% (w/v) SDS at 60° C. for 30 minutes.

"Complementary," as used herein, refers to the capacity for precise pairing between two nucleotides on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which are used to indicate a sufficient degree of precise pairing or complementarity over a sufficient number of nucleotides such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense compound which is 18 nucleotides in length having 4 (four) noncomplementary nucleotides which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., (1990) *J. Mol. Biol.*, 215, 403-410; Zhang and Madden, (1997) *Genome Res.*, 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.*, (1981) 2, 482-489).

As used herein, the term "Thermal Melting Point (Tm)" refers to the temperature, under defined ionic strength, pH, and nucleic acid concentration, at which 50% of the oligonucleotides complementary to the target sequence hybridize to the target sequence at equilibrium. Typically, stringent conditions will be those in which the salt concentration is at least about 0.01 to 1.0 M Na ion concentration (or other salts) at pH 7.0 to 8.3 and the temperature is at least about 30° C. for short oligonucleotides (e.g., 10 to 50 nucleotide). Stringent may also be achieved with the addition of destabilizing agents such as formamide.

As used herein, "modulation" means either an increase (stimulation) or a decrease (inhibition) in the expression of a gene.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of as given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radioisotope, fluorescent, and enzyme label.

As used herein, the term "animal" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

As used herein, the term "cancer" refers to any malignant tumor, particularly arising in the lung, kidney, or thyroid. The cancer manifests itself as a "tumor" or tissue comprising malignant cells of the cancer. Examples of tumors include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. As noted above, the invention specifically permits differential diagnosis of lung, kidney, and thyroid tumors.

Polynucleotide and Oligonucleotide Compositions and Molecules

Targets: In one embodiment, the targets comprise nucleic acid sequences of Vascular Endothelial Growth Factor (VEGF), including without limitation sense and/or antisense noncoding and/or coding sequences associated with VEGF.

Vascular Endothelial Growth Factor (VEGF) is a potent stimulating factor for angiogenesis and vascular permeability. There are eight isoforms with different and sometimes overlapping functions. The mechanisms of action are under investigation with emerging insights into overlapping pathways and cross-talk between other receptors such as the neurophilins, which were not previously associated to angiogenesis. VEGF has important physiological actions on the embryonic development, healing and menstrual cycle. It has also a great role in pathological conditions that are associated to autoimmune diseases.

Exemplary Vascular Endothelial Growth Factor mediated diseases and disorders which can be treated with cell/tissues regenerated from stem cells obtained using the antisense compounds comprise diseases that are characterized by excessive vascular endothelial cell proliferation; cardiovascular diseases which results from a cardiovascular insufficiency, (e.g., coronary artery disease, congestive heart failure, and peripheral vascular disease); Conditions that are characterized or caused by abnormal or excessive angiogenesis, include, but are not limited to: cancer (e.g., activation of oncogenes, loss of tumor suppressors); infectious diseases (e.g., pathogens express angiogenic genes, enhance angiogenic programs); autoimmune disorders (e.g., activation of mast cells and other leukocytes), including rheumatoid arthritis; vascular malformations (e.g., Tie-2 mutation); DiGeorge syndrome (e.g., low VEGF and neuropilin-1 expression); HHT (e.g., mutations of endoglin or LK-1), cavernous hemangioma (e.g., loss of Cx37 and Cx40); atherosclerosis; transplant ateriopathy; obesity (e.g., angiogenesis induced by fatty diet, weight loss by angiogenesis inhibitors); psoriasis; warts; allergic dermatitis; scar keloids; pyogenic granulomas; blistering disease; Kaposi sarcoma in AIDS patients; persistent hyperplastic vitreous syndrome (e.g., loss of Ang-2 or VEGF164); Autosomal dominant polycystic kidney disease (ADPKD); diabetic retinopathy; retinopathy of prematurity; age related macular degeneration; choroidal neovascularization (e.g., TIMP-3 mutation); primary pulmonary hypertension (e.g., germline BMPR-2 mutation, somatic EC mutation); asthma; nasal polyps; inflammatory bowel disease; nerve injury, brain injury and Neurodegenerative disorders (e.g. Alzheimer's disease, Parkinson's disease, amyotrophic lateral sclerosis etc.); periodontal disease; ascites; peritoneal adhesions; endometriosis; uterine bleeding; ovarian cysts; ovarian hyperstimulation; arthritis; synovitis; osteomyelitis; and/or osteophyte formation; ulceration; verruca vulgaris; angiofibroma of tuberous sclerosis; pot-wine stains; Sturge Weber syndrome; Kippel-Trenaunay-Weber syndrome; Osler-Weber-Rendu syndrome and any other diseases or conditions that are related to the levels of VEGF-R in a cell or tissue.

In a preferred embodiment, the oligonucleotides are specific for polynucleotides of VEGF, which includes, without limitation noncoding regions. The VEGF targets comprise variants of VEGF; mutants of VEGF, including SNPs; non-coding sequences of VEGF; alleles, fragments and the like. Preferably the oligonucleotide is an antisense RNA molecule.

In accordance with embodiments of the invention, the target nucleic acid molecule is not limited to VEGF polynucleotides alone but extends to any of the isoforms, receptors, homologs, non-coding regions and the like of VEGF.

In another preferred embodiment, an oligonucleotide targets a natural antisense sequence (natural antisense to the coding and non-coding regions) of VEGF targets, including, without limitation, variants, alleles, homologs, mutants, derivatives, fragments and complementary sequences thereto. Preferably the oligonucleotide is an antisense RNA or DNA molecule.

In another preferred embodiment, the oligomeric compounds of the present invention also include variants in which a different base is present at one or more of the nucleotide positions in the compound. For example, if the first nucleotide is an adenine, variants may be produced which contain thymidine, guanosine, cytidine or other natural or unnatural nucleotides at this position. This may be done at any of the positions of the antisense compound. These compounds are then tested using the methods described herein to determine their ability to inhibit expression of a target nucleic acid.

In some embodiments, homology, sequence identity or complementarity, between the antisense compound and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired. Such conditions include, i.e., physiological conditions in the case of in vivo assays or therapeutic treatment, and conditions in which assays are performed in the case of in vitro assays.

An antisense compound, whether DNA, RNA, chimeric, substituted etc, is specifically hybridizable when binding of the compound to the target DNA or RNA molecule interferes with the normal function of the target DNA or RNA to cause a loss of utility, and there is a sufficient degree of complementarily to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

In another preferred embodiment, targeting of VEGF including without limitation, antisense sequences which are identified and expanded, using for example, PCR, hybridization etc., one or more of the sequences set forth as SEQ ID NO.: 2, and the like, modulate the expression or function of VEGF. In one embodiment, expression or function is up-regulated as compared to a control. In another preferred embodiment, expression or function is down-regulated as compared to a control.

In another preferred embodiment, oligonucleotides comprise nucleic acid sequences set forth as SEQ ID NOS: 4 to 9 including antisense sequences which are identified, and expanded, using for example, PCR, hybridization etc. These oligonucleotides can comprise one or more modified nucleotides, shorter or longer fragments, modified bonds and the like. Examples of modified bonds or internucleotide linkages comprise phosphorothioate, phosphorodithioate or the like. In another preferred embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In embodiments of the present invention oligomeric antisense compounds, particularly oligonucleotides, bind to target nucleic acid molecules and modulate the expression and/or function of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The antisense compounds include antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes Vascular Endothelial Growth Factor (VEGF).

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

In a preferred embodiment, the antisense oligonucleotides bind to the natural antisense sequences of Vascular Endothelial Growth Factor (VEGF) and modulate the expression and/or function of Vascular Endothelial Growth Factor (VEGF) (SEQ ID NO: 1). Examples of antisense sequences include SEQ ID NOS: 2 to 9.

In another preferred embodiment, the antisense oligonucleotides bind to one or more segments of Vascular Endothelial Growth Factor (VEGF) polynucleotides and modulate the expression and/or function of Vascular Endothelial Growth Factor (VEGF). The segments comprise at least five consecutive nucleotides of the Vascular Endothelial Growth Factor (VEGF) sense or antisense polynucleotides.

In another preferred embodiment, the antisense oligonucleotides are specific for natural antisense sequences of Vascular Endothelial Growth Factor (VEGF) wherein binding of the oligonucleotides to the natural antisense sequences of Vascular Endothelial Growth Factor (VEGF) modulate expression and/or function of Vascular Endothelial Growth Factor (VEGF).

In another preferred embodiment, oligonucleotide compounds comprise sequences set forth as SEQ ID NOS: 4 to 9, antisense sequences which are identified and expanded, using for example, PCR, hybridization etc. These oligonucleotides can comprise one or more modified nucleotides, shorter or longer fragments, modified bonds and the like. Examples of modified bonds or internucleotide linkages comprise phosphorothioate, phosphorodithioate or the like. In another preferred embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG; and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding Vascular Endothelial Growth Factor (VEGF), regardless of the sequence(s) of such codons. A translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions that may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a targeted region is the intragenic region encompassing the translation initiation or termination codon of the open reading frame (ORF) of a gene.

Another target region includes the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene). Still another target region includes the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. Another target region for this invention is the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. In one embodiment, targeting splice sites, i.e., intron-exon junctions or exon-intron junctions, is particularly useful in situations where aberrant splicing is implicated in disease, or where an overproduction of a particular splice product is implicated in disease. An aberrant fusion junction due to rearrangement or deletion is another embodiment of a target site. mRNA transcripts produced via the process of splicing of two (or more) mRNAs from different gene sources are known as "fusion transcripts". Introns can be effectively targeted using antisense compounds targeted to, for example, DNA or pre-mRNA.

In another preferred embodiment, the antisense oligonucleotides bind to coding and/or non-coding regions of a target polynucleotide and modulate the expression and/or function of the target molecule.

In another preferred embodiment, the antisense oligonucleotides bind to natural antisense polynucleotides and modulate the expression and/or function of the target molecule.

In another preferred embodiment, the antisense oligonucleotides bind to sense polynucleotides and modulate the expression and/or function of the target molecule.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision alone or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also embodiments of target nucleic acids.

The locations on the target nucleic acid to which the antisense compounds hybridize are defined as at least a 5-nucleotide long portion of a target region to which an active antisense compound is targeted.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure.

Target segments 5-100 nucleotides in length comprising a stretch of at least five (5) consecutive nucleotides selected from within the illustrative preferred target segments are considered to be suitable for targeting as well.

Target segments can include DNA or RNA sequences that comprise at least the 5 consecutive nucleotides from the 5'-terminus of one of the illustrative preferred target segments (the remaining nucleotides being a consecutive stretch of the same DNA or RNA beginning immediately upstream of the 5'-terminus of the target segment and continuing until the DNA or RNA contains about 5 to about 100 nucleotides). Similarly preferred target segments are represented by DNA or RNA sequences that comprise at least the 5 consecutive nucleotides from the 3'-terminus of one of the illustrative preferred target segments (the remaining nucleotides being a consecutive stretch of the same DNA or RNA beginning immediately downstream of the 3'-terminus of the target segment and continuing until the DNA or RNA contains about 5 to about 100 nucleotides). One having skill in the art armed with the target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

In embodiments of the invention the oligonucleotides bind to an antisense strand of a particular target. The oligonucleotides are at least 5 nucleotides in length and can be synthesized so each oligonucleotide targets overlapping sequences such that oligonucleotides are synthesized to cover the entire length of the target polynucleotide. The targets also include coding as well as non coding regions.

In one embodiment, it is preferred to target specific nucleic acids by antisense oligonucleotides. Targeting an antisense compound to a particular nucleic acid, is a multistep process. The process usually begins with the identification of a nucleic acid sequence whose function is to be modulated. This may be, for example, a cellular gene (or mRNA transcribed from the gene) whose expression is associated with a particular disorder or disease state, or a non coding polynucleotide such as for example, non coding RNA (ncRNA).

RNAs can be classified into (1) messenger RNAs (mRNAs), which are translated into proteins, and (2) non-protein-coding RNAs (ncRNAs). ncRNAs comprise microRNAs, antisense transcripts and other Transcriptional Units (TU) containing a high density of stop codons and lacking any extensive "Open Reading Frame". Many ncRNAs appear to start from initiation sites in 3' untranslated regions (3'UTRs) of protein-coding loci. ncRNAs are often rare and at least half of the ncRNAs that have been sequenced by the FANTOM consortium seem not to be polyadenylated. Most researchers have for obvious reasons focused on polyadenylated mRNAs that are processed and exported to the cytoplasm. Recently, it was shown that the set of non-polyadenylated nuclear RNAs may be very large, and that many such transcripts arise from so-called intergenic regions (Cheng, J. et al. (2005) *Science* 308 (5725), 1149-1154; Kapranov, P. et al. (2005), *Genome Res* 15 (7), 987-997). The mechanism by which ncRNAs may regulate gene expression is by base pairing with target transcripts. The RNAs that function by base pairing can be grouped into (1) cis encoded RNAs that are encoded at the same genetic location, but on the opposite strand to the RNAs the act upon and therefore display perfect complementarity to their target, and (2) trans-encoded RNAs that are encoded at a chromosomal location distinct from the RNAs they act upon and generally do not exhibit perfect base-pairing potential with their targets.

Without wishing to be bound by theory, perturbation of an antisense polynucleotide by the antisense oligonucleotides described herein can alter the expression of the corresponding sense messenger RNAs. However, this regulation can either be discordant (antisense knockdown results in messenger RNA elevation) or concordant (antisense knockdown results in concomitant messenger RNA reduction). In these cases, antisense oligonucleotides can be targeted to overlapping or non-overlapping parts of the antisense transcript resulting in its knockdown or sequestration. Coding as well as non-coding antisense can be targeted in an identical manner and that either category is capable of regulating the corresponding sense transcripts—either in a concordant or disconcordant manner. The strategies that are employed in identifying new oligonucleotides for use against a target can be based on the knockdown of antisense RNA transcripts by antisense oligonucleotides or any other means of modulating the desired target.

Strategy 1: In the case of discordant regulation, knocking down the antisense transcript elevates the expression of the conventional (sense) gene. Should that latter gene encode for a known or putative drug target, then knockdown of its antisense counterpart could conceivably mimic the action of a receptor agonist or an enzyme stimulant.

Strategy 2: In the case of concordant regulation, one could concomitantly knock down both antisense and sense transcripts and thereby achieve synergistic reduction of the conventional (sense) gene expression. If, for example, an antisense oligonucleotide is used to achieve knockdown, then this strategy can be used to apply one antisense oligonucleotide targeted to the sense transcript and another antisense oligonucleotide to the corresponding antisense transcript, or a single energetically symmetric antisense oligonucleotide that simultaneously targets overlapping sense and antisense transcripts.

According to the present invention, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, doublestranded, circular or hairpin oligomeric compounds and may contain structural elements such as internal or terminal bulges, mismatches or loops.

Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression or function is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

In another preferred embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

dsRNA can also activate gene expression, a mechanism that has been termed "small RNA-induced gene activation" or RNAa. dsRNAs targeting gene promoters induce potent transcriptional activation of associated genes. RNAa was demonstrated in human cells using synthetic dsRNAs, termed "small activating RNAs" (saRNAs). It is currently not known whether RNAa is conserved in other organisms.

Small double-stranded RNA (dsRNA), such as small interfering RNA (siRNA) and microRNA (miRNA), have been found to be the trigger of an evolutionary conserved mechanism known as RNA interference (RNAi). RNAi invariably leads to gene silencing via remodeling chromatin to thereby suppress transcription, degrading complementary mRNA, or blocking protein translation. However, in instances described in detail in the examples section which follows, oligonucleotides are shown to increase the expression and/or function of the Vascular Endothelial Growth Factor (VEGF) polynucleotides and encoded products thereof. dsRNAs may also act as small activating RNAs (saRNA). Without wishing to be bound by theory, by targeting sequences in gene promoters, saRNAs would induce target gene expression in a phenomenon referred to as dsRNA-induced transcriptional activation (RNAa).

In a further embodiment, the "preferred target segments" identified herein may be employed in a screen for additional compounds that modulate the expression of Vascular Endothelial Growth Factor (VEGF) polynucleotides. "Modulators" are those compounds that decrease or increase the expression of a nucleic acid molecule encoding Vascular Endothelial Growth Factor (VEGF) and which comprise at least a 5-nucleotide portion that is complementary to a preferred target segment. The screening method comprises the steps of contacting a preferred target segment of a nucleic acid molecule encoding sense or natural antisense polynucleotides of Vascular Endothelial Growth Factor (VEGF) with one or more candidate modulators, and selecting for one or more candidate modulators which decrease or increase the expression of a nucleic acid molecule encoding Vascular Endothelial Growth Factor (VEGF) polynucleotides, e.g. SEQ ID NOS: 4 to 9 Once it is shown that the candidate modulator or modulators are capable of modulating (e.g. either decreasing or increasing) the expression of a nucleic acid molecule encoding Vascular Endothelial Growth Factor (VEGF) polynucleotides, the modulator may then be employed in further investigative studies of the function of Vascular Endothelial Growth Factor (VEGF) polynucleotides, or for use as a research, diagnostic, or therapeutic agent in accordance with the present invention.

Targeting the natural antisense sequence preferably modulates the function of the target gene. For example, the VEGF gene (NM_001025366.1, FIG. 2). In a preferred embodiment, the target is an antisense polynucleotide of the Vascular Endothelial Growth Factor A gene. In a preferred embodiment, an antisense oligonucleotide targets sense and/or natural antisense sequences of Vascular Endothelial Growth Factor (VEGF) polynucleotides (e.g. accession number (NM_001025366.1, FIG. 2), variants, alleles, isoforms, homologs, mutants, derivatives, fragments and complementary sequences thereto. Preferably the oligonucleotide is an antisense molecule and the targets include coding and noncoding regions of antisense and/or sense VEGF polynucleotides.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al., (1998) *Nature*, 391, 806-811; Timmons and Fire, (1998) *Nature*, 395, 854; Timmons et al., (2001) *Gene*, 263, 103-112; Tabara et al., (1998) *Science*, 282, 430-431; Montgomery et al., (1998) *Proc. Natl. Acad. Sci. USA*, 95, 15502-15507; Tuschl et al., (1999) *Genes Dev.*, 13, 3191-3197; Elbashir et al., (2001) *Nature*, 411, 494-498; Elbashir et al., (2011) *Genes Dev.* 15, 188-200). For example, such double-stranded moieties have been shown to inhibit the target by the classical hybridization of antisense strand of the duplex to the target, thereby triggering enzymatic degradation of the target (Tijsterman et al., (2002) *Science*, 295, 694-697).

In a preferred embodiment, an antisense oligonucleotide targets Vascular Endothelial Growth Factor (VEGF) polynucleotides (e.g. accession number NM_001025366.1), variants, alleles, isoforms, homologs, mutants, derivatives, fragments and complementary sequences thereto. Preferably the oligonucleotide is an antisense molecule.

In accordance with embodiments of the invention, the target nucleic acid molecule is not limited to Vascular Endothelial Growth Factor (VEGF) alone but extends to any of the isoforms, receptors, homologs and the like of Vascular Endothelial Growth Factor (VEGF) molecules.

In another preferred embodiment, an oligonucleotide targets a natural antisense sequence of VEGF polynucleotides, for example, polynucleotides set forth as SEQ ID NOS: 2 and 3, and any variants, alleles, homologs, mutants, derivatives, fragments and complementary sequences thereto. Examples of antisense oligonucleotides are set forth as SEQ ID NOS: 4 to 9.

In one embodiment, the oligonucleotides are complementary to or bind to nucleic acid sequences of Vascular Endothelial Growth Factor (VEGF) antisense, including without limitation noncoding sense and/or antisense sequences associated with Vascular Endothelial Growth Factor (VEGF) polynucleotides and modulate expression and/or function of Vascular Endothelial Growth Factor (VEGF) molecules.

In another preferred embodiment, the oligonucleotides are complementary to or bind to nucleic acid sequences of VEGF natural antisense, set forth as SEQ ID NOS: 2 and 3, and modulate expression and/or function of VEGF molecules.

In a preferred embodiment, oligonucleotides comprise sequences of at least 5 consecutive nucleotides of SEQ ID NOS: 4 to 9 and modulate expression and/or function of Vascular Endothelial Growth Factor (VEGF) molecules.

The polynucleotide targets comprise VEGF, including family members thereof, variants of VEGF; mutants of VEGF, including SNPs; noncoding sequences of VEGF; alleles of VEGF; species variants, fragments and the like. Preferably the oligonucleotide is an antisense molecule.

In another preferred embodiment, the oligonucleotide targeting Vascular Endothelial Growth Factor (VEGF) polynucleotides, comprise: antisense RNA, interference RNA (RNAi), short interfering RNA (siRNA); micro interfering RNA (miRNA); a small, temporal RNA (stRNA); or a short, hairpin RNA (shRNA); small RNA-induced gene activation (RNAa); or, small activating RNA (saRNA).

In another preferred embodiment, targeting of Vascular Endothelial Growth Factor (VEGF) polynucleotides, e.g. SEQ ID NOS: 2 and 3, modulates the expression or function of these targets. In one embodiment, expression or function is up-regulated as compared to a control. In another preferred embodiment, expression or function is down-regulated as compared to a control.

In another preferred embodiment, antisense compounds comprise sequences set forth as SEQ ID NOS: 4 to 9. These oligonucleotides can comprise one or more modified nucleotides, shorter or longer fragments, modified bonds and the like.

In another preferred embodiment, SEQ ID NOS: 4 to 9 comprise one or more LNA nucleotides.

The modulation of a desired target nucleic acid can be carried out in several ways known in the art. For example, antisense oligonucleotides, siRNA etc. Enzymatic nucleic acid molecules (e.g., ribozymes) are nucleic acid molecules capable of catalyzing one or more of a variety of reactions, including the ability to repeatedly cleave other separate nucleic acid molecules in a nucleotide base sequence-specific manner. Such enzymatic nucleic acid molecules can be used, for example, to target virtually any RNA transcript (Zaug et al., 324, *Nature* 429 1986; Cech, 260 *JAMA* 3030, 1988; and Jefferies et al., 17 *Nucleic Acids Research* 1371, 1989).

Because of their sequence-specificity, trans-cleaving enzymatic nucleic acid molecules show promise as therapeutic agents for human disease (Usman & McSwiggen, (1995) *Ann. Rep. Med. Chem.* 30, 285-294; Christoffersen and Marr, (1995) *J. Med. Chem.* 38, 2023-2037). Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, (1979) *Proc. R. Soc. London*, B 205, 435) have been used to evolve new nucleic acid catalysts capable of catalyzing a variety of reactions, such as cleavage and ligation of phosphodiester linkages and amide linkages, (Joyce, (1989) *Gene*, 82, 83-87; Beaudry et al., (1992) *Science* 257, 635-641; Joyce, (1992) *Scientific American* 267, 90-97; Breaker et al., (1994) *TIBTECH* 12, 268; Bartel et al., (1993) *Science* 261:1411-1418; Szostak, (1993) *TIBS* 17, 89-93; Kumar et al., (1995) *FASEB J.* 9, 1183; Breaker, (1996) *Curr. Op. Biotech.*, 7, 442).

The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min-1 in the presence of saturating (10 mM) concentrations of Mg2+ cofactor. An artificial "RNA ligase" ribozyme has been shown to catalyze the corresponding self-modification reaction with a rate of about 100 min-1. In addition, it is known that certain modified hammerhead ribozymes that have substrate binding arms made of DNA catalyze RNA cleavage with multiple turn-over rates that approach 100 min-1. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural self-cleaving ribozymes. It is then possible that the structures of certain selfcleaving ribozymes may be optimized to give maximal catalytic activity, or that entirely new RNA motifs can be made that display significantly faster rates for RNA phosphodiester cleavage.

Intermolecular cleavage of an RNA substrate by an RNA catalyst that fits the "hammerhead" model was first shown in 1987 (Uhlenbeck, O. C. (1987) *Nature*, 328: 596-600). The RNA catalyst was recovered and reacted with multiple RNA molecules, demonstrating that it was truly catalytic.

Catalytic RNAs designed based on the "hammerhead" motif have been used to cleave specific target sequences by making appropriate base changes in the catalytic RNA to maintain necessary base pairing with the target sequences (Haseloff and Gerlach, (1988) *Nature*, 334, 585; Walbot and Bruening, (1988) *Nature*, 334, 196; Uhlenbeck, O. C. (1987) *Nature*, 328: 596-600; Koizumi, M., et al. (1988) *FEBS Lett.*, 228: 228-230). This has allowed use of the catalytic RNA to cleave specific target sequences and indicates that catalytic RNAs designed according to the "hammerhead" model may possibly cleave specific substrate RNAs in vivo. (see Haseloff and Gerlach, (1988) *Nature*, 334, 585; Walbot and Bruening, (1988) *Nature*, 334, 196; Uhlenbeck, O. C. (1987) *Nature*, 328: 596-600).

RNA interference (RNAi) has become a powerful tool for modulating gene expression in mammals and mammalian cells. This approach requires the delivery of small interfering RNA (siRNA) either as RNA itself or as DNA, using an expression plasmid or virus and the coding sequence for small hairpin RNAs that are processed to siRNAs. This system enables efficient transport of the pre-siRNAs to the cytoplasm where they are active and permit the use of regulated and tissue specific promoters for gene expression.

In a preferred embodiment, an oligonucleotide or antisense compound comprises an oligomer or polymer of ribonucleic acid (RNA) and/or deoxyribonucleic acid (DNA), or a mimetic, chimera, analog or homolog thereof. This term includes oligonucleotides composed of naturally occurring nucleotides, sugars and covalent internucleoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

According to the present invention, the oligonucleotides or "antisense compounds" include antisense oligonucleotides (e.g. RNA, DNA, mimetic, chimera, analog or homolog thereof), ribozymes, external guide sequence (EGS) oligonucleotides, siRNA compounds, single- or double-stranded RNA interference (RNAi) compounds such as siRNA compounds, saRNA, aRNA, and other oligomeric compounds which hybridize to at least a portion of the target nucleic acid and modulate its function. As such, they may be DNA, RNA, DNA-like, RNA-like, or mixtures thereof, or may be mimetics of one of more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines (Hammond et al., (1991) *Nat. Rev. Genet.*, 2, 110-119; Matzke et al., (2001) *Curr. Opin. Genet. Dev.*, 11, 221-227; Sharp, (2001) *Genes Dev.*, 15, 485-490). When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

The antisense compounds in accordance with this invention can comprise an antisense portion from about 5 to about 80 nucleotides (i.e. from about 5 to about 80 linked nucleosides) in length. This refers to the length of the antisense strand or portion of the antisense compound. In other words, a single-stranded antisense compound of the invention comprises from 5 to about 80 nucleotides, and a double-stranded antisense compound of the invention (such as a dsRNA, for example) comprises a sense and an antisense strand or portion of 5 to about 80 nucleotides in length. One of ordinary skill in the art will appreciate that this comprehends antisense portions of 5, 6, 7,8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 79, or 80 nucleotides in length, or any range therewithin.

In one embodiment, the antisense compounds of the invention have antisense portions of 10 to 50 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length.

In one embodiment, the antisense or oligonucleotide compounds of the invention have antisense portions of 12 or 13 to 30 nucleotides in length. One having ordinary skill in the art will appreciate that this embodies antisense compounds having antisense portions of 12, 13, 14, 15, 16, 17, 18, 19, 20, 21, 22, 23, 24, 25, 26, 27, 28, 29 or 30 nucleotides in length, or any range therewithin.

In another preferred embodiment, the oligomeric compounds of the present invention also include variants in which a different base is present at one or more of the nucleotide positions in the compound. For example, if the first nucleotide is an adenosine, variants may be produced which contain thymidine, guanosine or cytidine at this position. This may be done at any of the positions of the antisense or dsRNA compounds. These compounds are then tested using the methods described herein to determine their ability to inhibit expression of a target nucleic acid.

In some embodiments, homology, sequence identity or complementarity, between the antisense compound and target is from about 40% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In another preferred embodiment, the antisense oligonucleotides, such as for example, nucleic acid molecules set forth in SEQ ID NOS: 4 to 9 comprise one or more substitutions or modifications. In one embodiment, the nucleotides are substituted with locked nucleic acids (LNA).

In another preferred embodiment, the oligonucleotides target one or more regions of the nucleic acid molecules sense and/or antisense of coding and/or non-coding sequences associated with VEGF and the sequences set forth as SEQ ID NOS: 1 to 3. The oligonucleotides are also targeted to overlapping regions of SEQ ID NOS: 1 to 3.

Certain preferred oligonucleotides of this invention are chimeric oligonucleotides. "Chimeric oligonucleotides" or "chimeras," in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense modulation of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one preferred embodiment, a chimeric oligonucleotide comprises at least one region modified to increase target binding affinity, and, usually, a region that acts as a substrate for RNAse H. Affinity of an oligonucleotide for its target (in this case, a nucleic acid encoding ras) is routinely determined by measuring the Tm of an oligonucleotide/target pair, which is the temperature at which the oligonucleotide and target dissociate; dissociation is detected spectrophotometrically. The higher the Tm, the greater is the affinity of the oligonucleotide for the target.

Chimeric antisense compounds of the invention may be formed as composite structures of two or more oligonucleotides, modified oligonucleotides, oligonucleosides and/or oligonucleotides mimetics as described above. Such; compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In another preferred embodiment, the region of the oligonucleotide which is modified comprises at least one nucleotide modified at the 2' position of the sugar, most preferably a 2'-Oalkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target. The effect of such increased affinity is to greatly enhance RNAi oligonucleotide inhibition of gene expression. RNAse H is a cellular endonuclease that cleaves the RNA strand of RNA:DNA duplexes; activation of this enzyme therefore results in cleavage of the RNA target, and thus can greatly enhance the efficiency of RNAi inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance. Some desirable modifications can be found in De Mesmaeker et al. (1995) *Acc. Chem. Res.*, 28:366-374.

Specific examples of some preferred oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2—NH—O—CH2, CH, —N(CH3)—O—CH2 [known as a methylene(methylimino) or MMI backbone], CH2—O—N(CH3)—CH2, CH2—N (CH3)—N(CH3)—CH2 and O—N(CH3)—CH2—CH2 backbones, wherein the native phosphodiester backbone is represented as O—P—O—CH,). The amide backbones disclosed by De Mesmaeker et al. (1995) *Acc. Chem. Res.* 28:366-374 are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleotides being bound directly or indirectly to the aza nitrogen atoms of the polyamide backbone (Nielsen et al. (1991) *Science* 254, 1497). Oligonucleotides may also comprise one or more substituted sugar moieties. Preferred oligonucleotides comprise one of the following at the 2' position: OH, SH, SCH3, F, OCN, OCH3OCH3, OCH3O(CH2)nCH3, O(CH2)nNH2 or O(CH2)nCH3 where n is from 1 to about 10; C1 to C10 lower alkyl, alkoxyalkoxy, substituted lower alkyl, alkaryl or aralkyl; Cl; Br; CN; CF3; OCF3; O—, S—, or N-alkyl; O—, S—, or N-alkenyl; SOCH3; SO2CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH2CH2OCH3, also known as 2'-O-(2-methoxyethyl)] (Martin et al., 1995) *Helv. Chim. Acta,* 78, 486). Other preferred modifications include 2'-methoxy (2'-O—CH3), 2'-propoxy (2'-OCH2CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleotides include adenine (A), guanine (G), thymine (T), cytosine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), hydroxymethylcytosine (HMC), glycosyl HMC and gentobiosyl HMC, as well as synthetic nucleotides, e.g., 2-aminoadenine, 2-(methylamino)adenine, 2-(imidazolylalkyl)adenine, 2-(aminoalkyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. (Kornberg A., DNA Replication, W. H. Freeman & Co., San Francisco, 1980, pp 75-77; Gebeyehu, G., (1987) et al. *Nucl. Acids Res.* 15:4513). A "universal" base known in the art, e.g., inosine, may be included, 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., (1989) *Proc. Natl. Acad. Sci. USA* 86, 6553), cholic acid (Manoharan et al. (1994) *Bioorg. Med. Chem. Let.* 4, 1053), a thioether, e.g., hexyl-S-tritylthiol (Manoharan et al. (1992) *Ann. N.Y. Acad. Sci.* 660, 306; Manoharan et al. (1993) *Bioorg. Med. Chem. Let.* 3, 2765), a thiocholesterol (Oberhauser et al., (1992) *Nucl. Acids Res.* 20, 533), an aliphatic chain, e.g., dodecandiol or undecyl residues (Saison-Behmoaras et al. EMBO J. 1991, 10, 111; Kabanov et al. (1990) *FEBS Lett.* 259, 327; Svinarchuk et al. (1993) *Biochimie* 75, 49), a phospholipid, e.g., di-hexadecyl-rac-glycerol or triethylammonium 1,2-di-O-hexadecyl-rac-glycero-3-H-phosphonate (Manoharan et al. (1995) *Tetrahedron Lett.* 36, 3651; Shea et al. (1990) *Nucl. Acids Res.* 18, 3777), a polyamine or a polyethylene glycol chain (Manoharan et al. (1995) *Nucleosides & Nucleotides,* 14, 969), or adamantane acetic acid (Manoharan et al. (1995) *Tetrahedron Lett.* 36, 3651). Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In accordance with the invention, use of modifications such as the use of LNA monomers to enhance the potency, specificity and duration of action and broaden the routes of administration of oligonucleotides comprised of current chemistries such as MOE, ANA, FANA, PS etc (Uhlman, et al. (2000) *Current Opinions in Drug Discovery & Development* Vol. 3 No 2). This can be achieved by substituting some of the monomers in the current oligonucleotides by LNA monomers. The LNA modified oligonucleotide may have a size similar to the parent compound or may be larger or preferably smaller. It is preferred that such LNA-modified oligonucleotides contain less than about 70%, more preferably less than about 60%, most preferably less than about 50% LNA monomers and that their sizes are between about 5 and 25 nucleotides, more preferably between about 12 and 20 nucleotides.

Preferred modified oligonucleotide backbones comprise, but not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus containing linkages comprise, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,221,131; 5,399,676; 5,405,939; 5,453,496; 5,455,213; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleosides comprise, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen, et al. (1991) *Science* 254, 1497-1500.

In another preferred embodiment of the invention the oligonucleotides with phosphorothioate backbones and oligonucleosides with heteroatom backbones, and in particular —CH2—NH—O—CH2—, —CH2—N(CH3)—O—CH2— known as a methylene (methylimino) or MMI backbone, —CH2—O—N(CH3)—CH2—, —CH2N(CH3)—N(CH3)CH2—and —O—N(CH3)—CH2—CH2—wherein the native phosphodiester backbone is represented as —O—P—O—CH2— of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O alkyl-O-alkyl, wherein the alkyl, alkenyl and alkynyl may be substituted or unsubstituted C to CO alkyl or C2 to CO alkenyl and alkynyl. Particularly preferred are O($CH_2$)n O$mCH_3$, O($CH_2$)n, O$CH_3$, O($CH_2$)n$NH_2$, O($CH_2$)n$CH_3$, O($CH_2$)nO$NH_2$, and O($CH_2$nON($CH_2$)n$CH_3$)2 where n and m can be from 1 to about 10. Other preferred oligonucleotides comprise one of the following at the 2' position: C to CO, (lower alkyl, substituted lower alkyl, alkaryl, aralkyl, O-alkaryl or O-aralkyl, SH, $SCH_3$, OCN, Cl, Br, CN, $CF_3$, O$CF_3$, SO$CH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification comprises 2'-methoxyethoxy (2'-O—$CH_2CH_2OCH_3$, also known as 2'-O-(2-methylethyl) or 2'-MOE) (Martin et al., (1995) *Helv. Chim. Acta,* 78, 486-504) i.e., an alkoxyalkoxy group. A further preferred modification comprises 2'-dimethylaminooxyethoxy, i.e., a O($CH_2$) 2ON($CH_3$)2 group, also known as 2'-DMAOE, as described in examples herein below, and 2'-dimethylaminoethoxy-ethoxy (also known in the art as 2'-O-dimethylaminoethoxy-ethyl or 2'-DMAEOE), i.e., 2'-O—$CH_2$-O—$CH_2$-N($CH_2$)2.

Other preferred modifications comprise 2'-methoxy (2'-O$CH_3$), 2'-aminopropoxy (2'-O$CH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures comprise, but are not limited to, U.S. Pat. Nos. 4,981,957; 5,118,800; 5,319, 080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference.

Oligonucleotides may also comprise nucleobase (often referred to in the art simply as "base") modifications or substitutions. As used herein, "unmodified" or "natural" nucleotides comprise the purine bases adenine (A) and guanine (G), and the pyrimidine bases thymine (T), cytosine (C) and uracil (U). Modified nucleotides comprise other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleotides comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., 'Angewandle Chemie, International Edition', 1991, 30, page 613, and those disclosed by Sanghvi, Y. S., Chapter 15, 'Antisense Research and Applications', pages 289-302, Crooke, S. T. and Lebleu, B. ea., CRC Press, 1993. Certain of these nucleotides are particularly useful for increasing the binding affinity of the oligomeric compounds of the invention. These comprise 5-substituted pyrimidines, 6-azapyrimidines and N-2, N-6 and 0-6 substituted purines, comprising 2-aminopropyladenine, 5-propynyluracil and 5-propynylcytosine, 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-Omethoxyethyl sugar modifications.

Representative United States patents that teach the preparation of the above noted modified nucleotides as well as other modified nucleotides comprise, but are not limited to, U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

Another modification of the oligonucleotides of the invention involves chemically linking to the oligonucleotide one or more moieties or conjugates, which enhance the activity, cellular distribution, or cellular uptake of the oligonucleotide.

Such moieties comprise but are not limited to, lipid moieties such as a cholesterol moiety (Letsinger et al., (1989) *Proc. Natl. Acad. Sci. USA,* 86, 6553-6556), cholic acid (Manoharan et al., (1994) *Bioorg. Med. Chem. Let.,* 4, 1053-1060), a thioether, e.g., hexyl-S-tritylthiol (Manoharan et al., (1992) *Ann. N. Y. Acad. Sci.,* 660, 306-309; Manoharan et al., (1993) *Bioorg. Med. Chem. Let.,* 3, 2765-2770), a thiocholesterol (Oberhauser et al., (1992) *Nucl. Acids Res.,* 20, 533-538), an aliphatic chain, e.g., dodocandiol or undecyl residues (Kabanov et al., (1990) *FEBS Lett.,* 259, 327-330; Svinarchuk et al., (1993) *Biochimie* 75, 49-54), a phospholipid, e.g., di-hexadecyl-rac-glycerol or triethylammonium 1,2-di-O-hexadecyl-rac-glycero-3-H-phosphonate (Manoharan et al., (1995) *Tetrahedron Lett.,* 36, 3651-3654; Shea et al., (1990) *Nucl. Acids Res.,* 18, 3777-3783), a polyamine or a polyethylene glycol chain (Manoharan et al., (1995) Nucleosides & Nucleotides, 14, 969-973), or adamantane acetic acid (Manoharan et al., (1995) *Tetrahedron Lett.,* 36, 3651-3654), a palmityl moiety (Mishra et al., (1995) *Biochim. Biophys. Acta,* 1264, 229-237), or an octadecylamine or hexylamino-carbonyl-t oxycholesterol moiety (Crooke et al., (1996) *J. Pharmacol. Exp. Ther.,* 277, 923-937).

Representative United States patents that teach the preparation of such oligonucleotides conjugates comprise, but are not limited to, U.S. Pat. Nos. 4,828,979; 4,948,882; 5,218, 105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,171,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Drug discovery: The compounds of the present invention can also be applied in the areas of drug discovery and target validation. The present invention comprehends the use of the compounds and preferred target segments identified herein in drug discovery efforts to elucidate relationships that exist between Vascular Endothelial Growth Factor (VEGF) polynucleotides and a disease state, phenotype, or condition. These methods include detecting or modulating Vascular Endothelial Growth Factor (VEGF) polynucleotides comprising contacting a sample, tissue, cell, or organism with the compounds of the present invention, measuring the nucleic acid or protein level of Vascular Endothelial Growth Factor (VEGF) polynucleotides and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

Assessing Up-Regulation or Inhibition of Gene Expression:

Transfer of an exogenous nucleic acid into a host cell or organism can be assessed by directly detecting the presence of the nucleic acid in the cell or organism. Such detection can be achieved by several methods well known in the art. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods including gene expression analysis. For instance, mRNA produced from an exogenous nucleic acid can be detected and quantified using a Northern blot and reverse transcription PCR (RT-PCR).

Expression of RNA from the exogenous nucleic acid can also be detected by measuring an enzymatic activity or a reporter protein activity. For example, antisense modulatory activity can be measured indirectly as a decrease or increase in target nucleic acid expression as an indication that the exogenous nucleic acid is producing the effector RNA. Based on sequence conservation, primers can be designed and used to amplify coding regions of the target genes. Initially, the most highly expressed coding region from each gene can be used to build a model control gene, although any coding or non coding region can be used. Each control gene is assembled by inserting each coding region between a reporter coding region and its poly(A) signal. These plasmids would produce an mRNA with a reporter gene in the upstream portion of the gene and a potential RNAi target in the 3' non-coding region. The effectiveness of individual antisense oligonucleotides would be assayed by modulation of the reporter gene. Reporter genes useful in the methods of the present invention include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

Kits, Research Reagents, Diagnostics, and Therapeutics

The compounds of the present invention can be utilized for diagnostics, therapeutics, and prophylaxis, and as research reagents and components of kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics and in various biological systems, the compounds of the present invention, either alone or in combination with other compounds or therapeutics, are useful as tools in differential and/or combinatorial analyses to elucidate expression patterns of a portion or the entire complement of genes expressed within cells and tissues.

As used herein the term "biological system" or "system" is defined as any organism, cell, cell culture or tissue that expresses, or is made competent to express products of the Vascular Endothelial Growth Factor (VEGF) genes. These include, but are not limited to, humans, transgenic animals, cells, cell cultures, tissues, xenografts, transplants and combinations thereof.

As one non limiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, (2000) *FEBS Lett.*, 480, 17-24; Celis, et al., (2000) *FEBS Lett.*, 480, 2-16), SAGE (serial analysis of gene expression) (Madden, et al., (2000) Drug Discov. Today, 5, 415-425), READS (restriction enzyme amplification of digested cDNAs) (Prashar and Weissman, (1999) *Methods Enzymol.*, 303, 258-72), TOGA (total gene expression analysis) (Sutcliffe, et al., (2000) *Proc. Natl. Acad. Sci. U.S.A.*, 97, 1976-81), protein arrays and proteomics (Celis, et al., (2000) *FEBS Lett.*, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., (2000) Anal. Biochem. 286, 91-98; Larson, et al., (2000) *Cytometry* 41, 203-208), subtractive cloning, differential display (DD) (Jurecic and Belmont, (2000) *Curr. Opin. Microbiol.* 3, 316-21), comparative genomic hybridization (Carulli, et al., (1998) *J. Cell Biochem. Suppl.*, 31, 286-96), FISH (fluorescent in situ hybridization) techniques (Going and Gusterson, (1999) *Eur. J. Cancer*, 35, 1895-904) and mass spectrometry methods (To, Comb, (2000) *Chem. High Throughput Screen*, 3, 235-41).

The compounds of the invention are useful for research and diagnostics, because these compounds hybridize to nucleic acids encoding Vascular Endothelial Growth Factor (VEGF). For example, oligonucleotides that hybridize with such efficiency and under such conditions as disclosed herein as to be effective Vascular Endothelial Growth Factor (VEGF) modulators are effective primers or probes under conditions favoring gene amplification or detection, respectively. These primers and probes are useful in methods requiring the specific detection of nucleic acid molecules encoding Vascular Endothelial Growth Factor (VEGF) and in the amplification of said nucleic acid molecules for detection or for use in further studies of Vascular Endothelial Growth Factor (VEGF). Hybridization of the antisense oligonucleotides, particularly the primers and probes, of the invention with a nucleic acid encoding Vascular Endothelial Growth Factor (VEGF) can be detected by means known in the art. Such means may include conjugation of an enzyme to the oligonucleotide, radiolabeling of the oligonucleotide, or any other suitable detection means. Kits using such detection means for detecting the level of Vascular Endothelial Growth Factor (VEGF) in a sample may also be prepared.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of Vascular Endothelial Growth Factor (VEGF) polynucleotides is treated by administering antisense compounds in accordance with this invention. For example, in one non-limiting embodiment, the methods comprise the step of administering to the animal in need of treatment, a therapeutically effective amount of Vascular Endothelial Growth Factor (VEGF) modulator. The Vascular Endothelial Growth Factor (VEGF) modulators of the present invention effectively modulate the activity of the Vascular Endothelial Growth Factor (VEGF) or modulate the expression of the Vascular Endothelial Growth Factor (VEGF) protein. In one embodiment, the activity or expression of Vascular Endothelial Growth Factor (VEGF) in an animal is inhibited by about 10% as compared to a control. Preferably, the activity or expression of Vascular Endothelial Growth Factor (VEGF) in an animal is inhibited by about 30%. More preferably, the activity or expression of Vascular Endothelial Growth Factor (VEGF) in an animal is inhibited by 50% or more. Thus, the oligomeric compounds modulate expression of Vascular Endothelial Growth Factor (VEGF) mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

In one embodiment, the activity or expression of Vascular Endothelial Growth Factor (VEGF) and/or in an animal is increased, by about 10% as compared to a control. Preferably, the activity or expression of Vascular Endothelial Growth Factor (VEGF) in an animal is increased by about 30%. More preferably, the activity or expression of Vascular Endothelial Growth Factor (VEGF) in an animal is increased by 50% or more. Thus, the oligomeric compounds modulate expression of Vascular Endothelial Growth Factor (VEGF) mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

For example, the reduction of the expression of Vascular Endothelial Growth Factor (VEGF) may be measured in serum, blood, adipose tissue, liver or any other body fluid, tissue or organ of the animal. Preferably, the cells contained within said fluids, tissues or organs being analyzed contain a nucleic acid molecule encoding Vascular Endothelial Growth Factor (VEGF) peptides and/or the Vascular Endothelial Growth Factor (VEGF) protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

Conjugates

Another modification of the oligonucleotides of the invention involves chemically linking to the oligonucleotide one or more moieties or conjugates that enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-Hphosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Representative United States patents that teach the preparation of such oligonucleotides conjugates include, but are not limited to, U.S. Pat. Nos. 4,828,972; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,165; 5,547,912; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Although, the antisense oligonucleotides do not need to be administered in the context of a vector in order to modulate a target expression and/or function, embodiments of the invention relates to expression vector constructs for the expression of antisense oligonucleotides, comprising promoters, hybrid promoter gene sequences and possess a strong constitutive promoter activity, or a promoter activity which can be induced in the desired case.

In an embodiment, invention practice involves administering at least one of the foregoing antisense oligonucleotides with a suitable nucleic acid delivery system. In one embodiment, that system includes a non-viral vector operably linked to the polynucleotide. Examples of such nonviral vectors include the oligonucleotide alone (e.g. any one or more of SEQ ID NOS: 4 to 9) or in combination with a suitable protein, polysaccharide or lipid formulation.

Additionally suitable nucleic acid delivery systems include viral vector, typically sequence from at least one of an adenovirus, adenovirus-associated virus (AAV), helper-dependent adenovirus, retrovirus, or hemagglutinatin virus of Japan-liposome (HVJ) complex. Preferably, the viral vector comprises a strong eukaryotic promoter operably linked to the polynucleotide e.g., a cytomegalovirus (CMV) promoter.

Additionally preferred vectors include viral vectors, fusion proteins and chemical conjugates. Retroviral vectors include Moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex 1 virus (HSV) vector [Geller, A. I. et al., (1995) *J. Neurochem*, 64: 487; Lim, F., et al., in DNA Cloning: Mammalian Systems, D. Glover, Ed. (Oxford Univ. Press, Oxford England) (1995); Geller, A. I. et al., (1993) *Proc Natl. Acad. Sci.:* U.S.A.: 90 7603; Geller, A. I., et al., (1990) *Proc Natl. Acad. Sci USA:* 87:1149], Adenovirus Vectors (LeGal LaSalle et al., Science, 259:988 (1993); Davidson, et al., (1993) *Nat. Genet.* 3: 219; Yang, et al., (1995) *J. Virol.* 69: 2004) and Adeno-associated Virus Vectors (Kaplitt, M. G., et al., (1994) *Nat. Genet.* 8:148).

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein by reference.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogeneous systems of one liquid dispersed in another in the form of droplets usually exceeding 0.1 µm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids. When incorporated into liposomes, these specialized lipids result in liposomes with enhanced circulation lifetimes relative to liposomes lacking such specialized lipids. Examples of stericallly stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein by reference.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of live broad categories, i.e., surfactants, fatty acids, bile salts, chelating agents, and non-chelating nonsurfactants. Penetration enhancers and their uses are further described in U.S. Pat. No. 6,287,860, which is incorporated herein by reference.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoyl-phosphatidyl DOPE ethanolamine, dimyristoylphosphatidyl choline DMPC, distearoylphosphatidyl choline) negative (e.g. dimyristoylphosphatidyl glycerol DMPG) and cationic (e.g. dioleoyltetramethylaminopropyl DOTAP and dioleoyl-phosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287, 860, which is incorporated herein by reference. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein by reference.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bischloroethyl-nitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclo-phosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. For example, the first target may be a particular antisense sequence of Vascular Endothelial Growth Factor (VEGF), and the second target may be a region from another nucleotide sequence. Alternatively, compositions of the invention may contain two or more antisense compounds targeted to different regions of the same Vascular Endothelial Growth Factor (VEGF) nucleic acid target. Numerous examples of antisense compounds are illustrated herein and others may be selected from among suitable compounds known in the art. Two or more combined compounds may be used together or sequentially.

Dosing:

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1

Design of Antisense Oligonucleotides Specific for a Nucleic Acid Molecule Antisense to and/or Sense Strand of Vascular Endothelial Growth Factor (VEGF) Polynucleotide As indicated above the term "oligonucleotide specific for" or "oligonucleotide targets" refers to an oligonucleotide having a sequence (i) capable of forming a stable complex with a portion of the targeted gene, or (ii) capable of forming a stable duplex with a portion of an mRNA transcript of the targeted gene.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e. under physiological conditions in the case of in vivo assays or therapeutic treatment, and under conditions in which assays are performed in the case of in vitro assays The hybridization properties of the oligonucleotides described herein can be determined by one or more in vitro assays as known in the art. For example, the properties of the oligonucleotides described herein can be obtained by determination of binding strength between the target natural antisense and a potential drug molecules using melting curve assay.

The binding strength between the target natural antisense and a potential drug molecule (Molecule) can be estimated using any of the established methods of measuring the strength of intermolecular interactions, for example, a melting curve assay.

Melting curve assay determines the temperature at which a rapid transition from double-stranded to single-stranded conformation occurs for the natural antisense/Molecule complex. This temperature is widely accepted as a reliable measure of the interaction strength between the two molecules.

A melting curve assay can be performed using a cDNA copy of the actual natural antisense RNA molecule or a synthetic DNA or RNA nucleotide corresponding to the binding site of the Molecule. Multiple kits containing all necessary reagents to perform this assay are available (e.g. Applied Biosystems Inc. MeltDoctor kit). These kits include a suitable buffer solution containing one of the double strand DNA (dsDNA) binding dyes such as ABI HRM dyes, SYBR Green, SYTO, etc.). The properties of the dsDNA dyes are such that they emit almost no fluorescence in free form, but are highly fluorescent when bound to dsDNA.

To perform the assay the cDNA or a corresponding oligonucleotide are mixed with Molecule in concentrations defined by the particular manufacturer's protocols. The mixture is heated to 95° C. to dissociate all pre-formed dsDNA complexes, then slowly cooled to room temperature or other lower temperature defined by the kit manufacturer to allow the DNA molecules to anneal. The newly formed complexes are then slowly heated to 95° C. with simultaneous continuous collection of data on the amount of fluorescence that is produced by the reaction. The fluorescence intensity is inversely proportional to the amounts of dsDNA present in the reaction. The data can be collected using a real time PCR instrument compatible with the kit (e.g. ABI's StepOne Plus Real Time PCR System or LightTyper instrument, Roche Diagnostics, Lewes, UK).

Melting peaks are constructed by plotting the negative derivative of fluorescence with respect to temperature (−d (Fluorescence)/dT) on the y-axis) against temperature (x-axis) using appropriate software (for example LightTyper (Roche) or SDS Dissociation Curve, ABI). The data is analyzed to identify the temperature of the rapid transition from dsDNA complex to single strand molecules. This temperature is called Tm and is directly proportional to the strength of interaction between the two molecules. Typically, Tm will exceed 40° C.

Example 2

Modulation of VEGF Polynucleotides

HepG2 cells from ATCC (cat #HB-8065) were grown in growth media (MEM/EBSS (Hyclone cat #SH30024, or Mediatech cat #MT-10-010-CV)+10% FBS (Mediatech cat #MT35-011-CV)+penicillin/streptomycin (Mediatech cat #MT30-002-CI)) at 37° C. and 5% $CO_2$. One day before the experiment the cells were replated at the density of $1.5 \times 10^5$/ml into 6 well plates and incubated at 37° C. and 5% $CO_2$. On the day of the experiment the media in the 6 well plates was changed to fresh growth media. All antisense oligonucleotides were diluted to the concentration of 20 μM. Two μl of this solution was incubated with 400 μl of Opti-MEM media (Gibco cat #31985-070) and 4 μl of Lipofectamine 2000 (Invitrogen cat #11668019) at room temperature for 20 min and applied to each well of the 6 well plates with HepG2 cells. Similar mixture including 2 μl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB14538) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs00173626_m1 by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Primers and probe for the custom designed Taqman assay for the VEGF natural antisense VEGFA (SEQ ID NO: 10) (FIG. 6)

```
Target sequence VEGFA exon 1:
                                      (SEQ ID NO: 10)
ATGCCAAGTGGTCCCAGGCTGCACC Forward Primer Sequence
Vegfas1 ANYf:
                                      (SEQ ID NO: 11)
GTAGCCTGTCCCCTTCAAGAG Vegfas2 ANYf:
                                      (SEQ ID NO: 12)
GCGGATAGCCTGGGAGCTA Reverse Primer Sequence
Vegfas1 ANYR:
                                      (SEQ ID NO: 13)
CAGACATCCTGAGGTGTGTTCT Vegfas2 ANYR:
                                      (SEQ ID NO: 14)
TGTTCGGTTGCTGTGACTGT Reporter Dye: FAM
Vegfas1 ANYM1:
                                      (SEQ ID NO: 15)
ATGCCTGCCAAGCCCA Vegfas2 ANYM1:
                                      (SEQ ID NO: 16)
CAGCCAGCCCTCTGC
```

Results:

VEGFAas RNA Downregulation

Figure 1B:
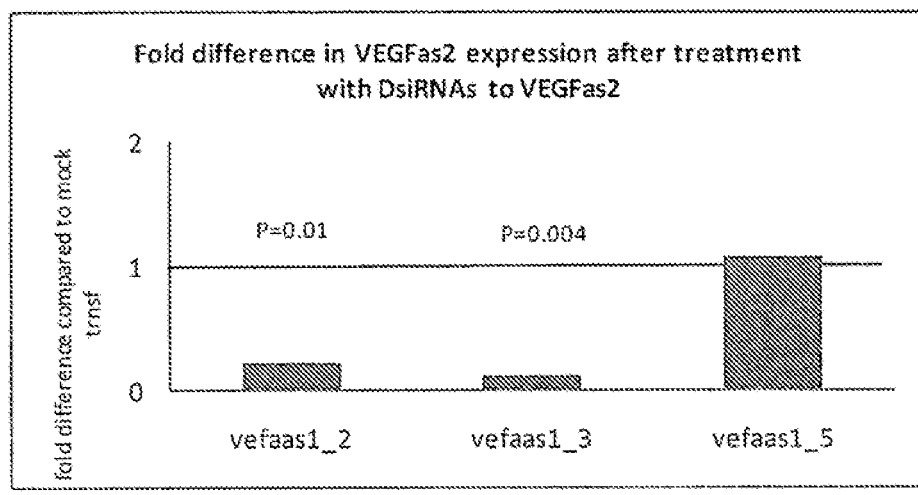

Real time PCR results show that the levels of the VEGFA mRNA in HepG2 cells are significantly increased 48 h after treatment with one of the siRNAs designed to vegfaas (vefaas1_2, P=0.05), and possibly with the second, vefaas1_3 (P=0.1, FIG. 1A). In the same samples the levels of vegfaas RNA were significantly decreased after treatment with either vefaas1_2 or vefaas1_3, but unchanged after treatment with vefaas1_5, which also had no effect on the VEGFA mRNA levels (FIG. 1B).

VEGRas RNA Downregulation

Figure 1C:
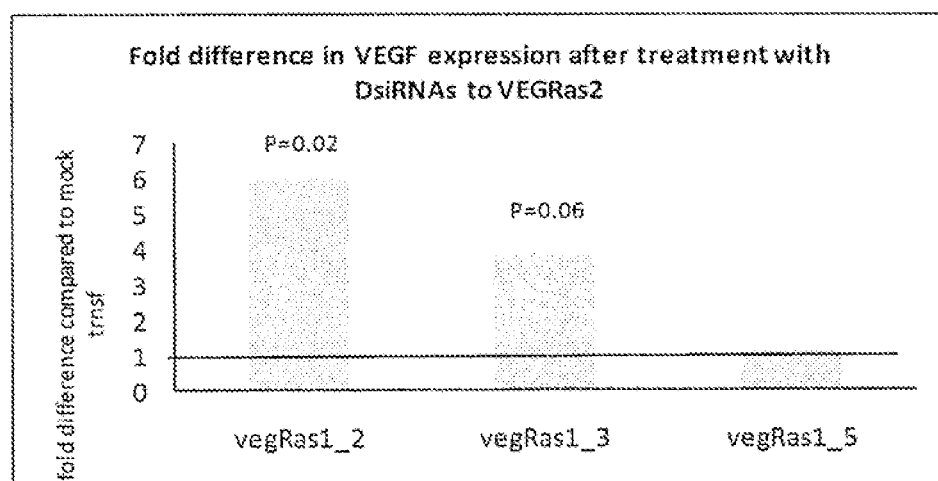

Real time PCR results show that the levels of the VEGFA mRNA in HepG2 cells are significantly increased 48 h after treatment with two of the siRNAs designed to vegRas (vegRas1_2, P=0.02 and vegRas1_3, P=0.06, FIG. 1C). The results for the change in vegRas RNA levels are pending.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

What is claimed is:

1. A synthetic, modified oligonucleotide of 15 to 30 nucleotides in length comprising at least one modification wherein the modification comprises at least one internucleotide linkage of: alkylphosphonate, phosphorothioate, phosphorodithioate, alkylphosphonothioate, phosphoramidate, carbamate, carbonate, phosphate triester, acetamidate, carboxymethyl ester, or combinations thereof, wherein said oligonucleotide is an antisense compound which specifically hybridizes and is at least 90% complementary to a human natural antisense polynucleotide of a Vascular Endothial Growth Factor gene and upregulates expression and/or function of said Vascular Endothelial Growth Factor (VEGF) gene in vivo or in vitro as compared to a control.

2. The oligonucleotide of claim 1, wherein the at least one modification comprises a combination of phosphorothioate internucleotide linkages and at least one internucleotide linkage selected from the group consisting of: alkylphosphonate, phosphorodithioate, alkylphosphonothioate, phosphoramidate, carbamate, carbonate, phosphate triester, acetamidate, carboxymethyl ester, and/or combinations thereof.

3. The oligonucleotide of claim 1, wherein said oligonucleotide comprises at least one phosphorothioate internucleotide linkage.

4. The oligonucleotide of claim 1, wherein said oligonucleotide comprising a backbone of phosphorothioate internucleotide linkages.

5. The oligonucleotide of claim 1, wherein the oligonucleotide optionally comprises at least one modified nucleotide comprising, peptide nucleic acids, locked nucleic acid (LNA) molecules, analogues, derivatives and/or combinations thereof.

6. The oligonucleotide of claim 1, wherein the oligonucleotide comprises a modified sugar moiety comprising a 2'-O-methoxyethyl modified sugar moiety, a 2'-methoxy modified sugar moiety, a 2'-O-alkyl modified sugar moiety, or a bicyclic sugar moiety.

7. The oligonucleotide of claim 1, wherein the oligonucleotides comprise the sequences set forth as SEQ ID NOS: 4 to 9.

8. A composition comprising one or more oligonucleotides according to claim 1 and a pharmaceutically acceptable excipient.

9. The composition of claim 8, wherein the oligonucleotides comprise a nucleotide sequence identity of at least about 90% as compared to any one of the nucleotide sequences set forth as SEQ ID NOS: 4 to 9.

10. The composition of claim 8, wherein the oligonucleotides comprise nucleotide sequences set forth as SEQ ID NOS: 4 to 9.

11. The composition of claim 10, wherein the oligonucleotides set forth as SEQ ID NOS: 4 to 9 comprise one or more modified or substituted nucleotides.

12. The composition of claim 8, wherein the modified nucleotides comprise modified bases comprising phosphorthiorate, methylphosphonate, peptide nucleic acids, locked nucleic acid (LNA) molecules.

* * * * *

SEQUENCE LISTING

<160> NUMBER OF SEQ ID NOS: 17

<210> SEQ ID NO 1
<211> LENGTH: 3665
<212> TYPE: DNA
<213> ORGANISM: Homo sapiens

<400> SEQUENCE: 1

| | | | | | |
|---|---|---|---|---|---|
| ggcttggggc | agccgggtag | ctcggaggtc | gtggcgctgg | gggctagcac | cagcgctctg | 60 |
| tcgggaggcg | cagcggttag | gtggaccggt | cagcggactc | accggccagg | gcgctcggtg | 120 |
| ctggaatttg | atattcattg | atccgggttt | tatccctctt | cttttttctt | aaacattttt | 180 |
| ttttaaaact | gtattgtttc | tcgttttaat | ttattttttgc | ttgccattcc | ccacttgaat | 240 |
| cgggccgacg | gcttggggag | attgctctac | ttccccaaat | cactgtggat | tttggaaacc | 300 |
| agcagaaaga | ggaaagaggt | agcaagagct | ccagagagaa | gtcgaggaag | agagagacgg | 360 |
| ggtcagagag | agcgcgcggg | cgtgcgagca | gcgaaagcga | caggggcaaa | gtgagtgacc | 420 |
| tgcttttggg | ggtgaccgcc | ggagcgcggc | gtgagccctc | cccttggga | tcccgcagct | 480 |
| gaccagtcgc | gctgacggac | agacagacag | acaccgcccc | cagccccagc | taccacctcc | 540 |
| tccccggccg | gcggcggaca | gtggacgcgg | cggcgagccg | cgggcagggg | ccggagcccg | 600 |
| cgcccggagg | cggggtggag | ggggtcgggg | ctcgcggcgt | cgcactgaaa | cttttcgtcc | 660 |
| aacttctggg | ctgttctcgc | ttcggaggag | ccgtggtccg | cgcggggaa | gccgagccga | 720 |
| gcggagccgc | gagaagtgct | agctcgggcc | gggaggagcc | gcagccggag | gaggggagg | 780 |
| aggaagaaga | gaaggaagag | gagaggggc | cgcagtggcg | actcggcgct | cggaagccgg | 840 |
| gctcatggac | gggtgaggcg | gcggtgtgcg | cagacagtgc | tccagccgcg | cgcgctcccc | 900 |
| aggccctggc | ccgggcctcg | ggccggggag | gaaagagtagc | tcgccgaggc | gccgaggaga | 960 |
| gcgggccgcc | ccacagcccg | agccggagag | ggagcgcgag | ccgcgccggc | cccggtcggg | 1020 |
| cctccgaaac | catgaacttt | ctgctgtctt | gggtgcattg | gagccttgcc | ttgctgctct | 1080 |
| acctccacca | tgccaagtgg | tcccaggctg | cacccatggc | agaaggagga | gggcagaatc | 1140 |
| atcacgaagt | ggtgaagttc | atggatgtct | atcagcgcag | ctactgccat | ccaatcgaga | 1200 |
| ccctggtgga | catcttccag | gagtaccctg | atgagatcga | gtacatcttc | aagccatcct | 1260 |
| gtgtgcccct | gatgcgatgc | gggggctgct | gcaatgacga | gggcctggag | tgtgtgccca | 1320 |
| ctgaggagtc | caacatcacc | atgcagatta | tgcggatcaa | acctcaccaa | ggccagcaca | 1380 |
| taggagagat | gagcttccta | cagcacaaca | aatgtgaatg | cagaccaaag | aaagatagag | 1440 |
| caagacaaga | aaaaaaatca | gttcgaggaa | agggaaaggg | gcaaaaacga | agcgcaaga | 1500 |
| aatcccggta | taagtcctgg | agcgtgtacg | ttggtgcccg | ctgctgtcta | atgccctgga | 1560 |
| gcctccctgg | ccccatccc | tgtgggcctt | gctcagagcg | gagaaagcat | ttgtttgtac | 1620 |
| aagatccgca | gacgtgtaaa | tgttcctgca | aaaacacaga | ctcgcgttgc | aaggcgaggc | 1680 |
| agcttgagtt | aaacgaacgt | acttgcagat | gtgacaagcc | gaggcggtga | gccgggcagg | 1740 |
| aggaaggagc | ctccctcagg | gtttcgggaa | ccagatctct | caccaggaaa | gactgataca | 1800 |
| gaacgatcga | tacagaaacc | acgctgccgc | caccacacca | tcaccatcga | cagaacagtc | 1860 |
| cttaatccag | aaacctgaaa | tgaaggaaga | ggagactctg | cgcagagcac | tttgggtccg | 1920 |
| gagggcgaga | ctccgcgga | agcattcccg | ggcgggtgac | ccagcacggt | ccctcttgga | 1980 |
| attggattcg | ccatttattt | tttcttgctg | ctaaatcacc | gagcccggaa | gattagagag | 2040 |
| ttttattttct | gggattcctg | tagacacacc | cacccacata | catacattta | tatatatata | 2100 |

```
tattatatat atataaaaat aaatatctct attttatata tataaaatat atatattctt    2160 ttttaaatt aacagtgcta atgttattgg tgtcttcact ggatgtattt gactgctgtg     2220
gacttgagtt gggaggggaa tgttcccact cagatcctga cagggaagag gaggagatga    2280
gagactctgg catgatcttt ttttgtccc acttggtggg gccagggtcc tctcccctgc     2340
ccaggaatgt gcaaggccag ggcatggggg caaatatgac ccagttttgg gaacaccgac    2400
aaacccagcc ctggcgctga gcctctctac cccaggtcag acggacagaa agacagatca    2460
caggtacagg gatgaggaca ccggctctga ccaggagttt ggggagcttc aggacattgc    2520
tgtgctttgg ggattccctc acatgctgc acgcgcatct cgcccccagg ggcactgcct     2580
ggaagattca ggagcctggg cggccttcgc ttactctcac ctgcttctga gttgcccagg    2640
agaccactgg cagatgtccc ggcgaagaga agagacacat tgttggaaga agcagcccat    2700
gacagctccc cttcctggga ctcgccctca tcctcttcct gctcccctc ctggggtgca     2760 gcctaaaagg acctatgtcc tcacaccatt gaaaccacta gttctgtccc ccaggagac    2820 ctggttgtgt gtgtgtgagt ggttgacctt cctccatccc ctggtccttc ccttcccttc    2880
ccgaggcaca gagagacagg gcaggatcca cgtgcccatt gtggaggcag agaaaagaga    2940
aagtgtttta tacggtac ttatttaata tcccttttta attagaaatt aaaacagtta      3000 attaattaa agagtagggt ttttttttcag tattcttggt taatatttaa tttcaactat    3060
ttatgagatg tatcttttgc tctctcttgc tctcttattt gtaccggttt ttgtatataa    3120
aattcatgtt tccaatctct ctctccctga tcggtgacag tcactagctt atcttgaaca    3180
gatatttaat tttgctaaca ctcagctctg ccctccccga tccctggct ccccagcaca     3240 cattcctttg aaataaggtt tcaatataca tctacatact atatatatat ttggcaactt    3300
gtatttgtgt gtatatatat atatatatgt ttatgtatat atgtgattct gataaaatag    3360
acattgctat tctgtttttt atatgtaaaa acaaaacaag aaaaaataga gaattctaca    3420
tactaaatct ctctccttttt ttaattttaa tatttgttat catttattta ttggtgctac   3480 tgttatccg taataattgt gggaaaaga tattaacatc acgtctttgt ctctagtgca      3540 gttttttcgag atattccgta gtacatattt attttaaac aacgacaaag aaatacagat    3600
atatcttaaa aaaaaaaag catttttgtat taagaatttt aattctgatc tcaaaaaaaa    3660
aaaaa                                                               3665

<210> SEQ ID NO 2
<211> LENGTH: 643
<212> TYPE: DNA
<213> ORGANISM: Homo sapiens

<400> SEQUENCE: 2
gaacgtggtg atgcggtgct tgggagctgg cacggaacca agagcaacac cagcctgctc      60
agcacgacct ggactgggag gcaggctggg tgtcctggag ccctgggcag gcagcaggat     120
ggggtgggag ttaaggaggt ctggggagga gaggcttggg cggtacttgg cagggagttc    180
tctccccagc ctgtcaaagc ctgctacacc atctcaccag acactcttcc gagcccaggc    240
gagcccccta ctctccccat ggcagagcag tcatttgggg aaacaggaag gggggcaggc    300
tgtagcctgt cccctttcaag agaaccagag ctctccatgc ctgccaagcc caagagaaca    360
cacctcagga tgtctgtcac agggaagaaa ggaggggaa aaggggccag agagggcaag     420
tctgtccccc ttaggagaaa gcaccaaagg gtggaaggaa ggtttccgca tccctctgct    480
```

```
ctggaagctg ggagctgagg gaagaggcaa ggggttgagg cctggtgggg gcttcaatgt    540
ccgcacagcc gtggaggcag acaagatggt gtgggggaaa gggcagggca caggtgctct    600
ctctcagtct ctctttccct ggaagctctt ggtgatgcaa acg                      643
```

```
<210> SEQ ID NO 3
<211> LENGTH: 513
<212> TYPE: DNA
<213> ORGANISM: Homo sapiens
<220> FEATURE:
<221> NAME/KEY: misc_feature
<222> LOCATION: (2)..(2)
<223> OTHER INFORMATION: n is a, c, g, or t

<400> SEQUENCE: 3
```

```
antggagaca ggctgggatc agcactgctg gcactaccca gccacgccag atttaggtca     60
gggaaactcg ctgggaagga agaccccagg gtcttccctc cccagaggtg gagagcacag    120
gccacagtca gtggtgggga gagccagtgt gtccccagag aactggggag atccaaacca    180
caacggaaca aaaggcaggc ggactcgggg ttgggccgcg gggcggatag cctgggagct    240
acagccagcc ctctgctggc cgtgggaggg acagtcacag caaccgaaca tagtcaagtg    300
gggttatctc caccccaaa ggaatgcaaa ccaggaaagg gaggggagat cccattaggc     360
tgagccctct tccccagccc aggcttgggg aacagggggcg atggtagggg caagtggttt    420
ctgggtccct agccctgcgt gaaacgggtt ccagaccaaa gagccctgat gaaggcatgt    480
ctctatatac tctatccctc ttccccagcc cag                                 513
```

```
<210> SEQ ID NO 4
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 4
ctgagcaggc tggtgttgct cttggtt                                         27
```

```
<210> SEQ ID NO 5
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 5
acagacatcc tgaggtgtgt tctcttg                                         27
```

```
<210> SEQ ID NO 6
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 6
gtttgcatca ccaagagctt ccaggga                                         27
```

```
<210> SEQ ID NO 7
<211> LENGTH: 27
<212> TYPE: DNA
<213> ORGANISM: Artificial Sequence
<220> FEATURE:
<223> OTHER INFORMATION: Antisense oligonucleotide
```

-continued

```
<400> SEQUENCE: 7
cagcagtgct gatcccagcc tgtctcc                                        27

<210> SEQ ID NO 8
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 8
gtatatagag acatgccttc atcaggg                                        27

<210> SEQ ID NO 9
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 9
ggctggctgt agctcccagg ctatccg                                        27

<210> SEQ ID NO 10
<211> LENGTH: 25
<212> TYPE: DNA
<213> ORGANISM: Artificial Sequence
<220> FEATURE:
<223> OTHER INFORMATION: Antisense oligonucleotide

<400> SEQUENCE: 10
atgccaagtg gtcccaggct gcacc                                          25

<210> SEQ ID NO 11
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 11
gtagcctgtc cccttcaaga g                                              21

<210> SEQ ID NO 12
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 12
gcggatagcc tgggagcta                                                 19

<210> SEQ ID NO 13
<211> LENGTH: 22
<212> TYPE: DNA
<213> ORGANISM: Artificial Sequence
<220> FEATURE:
<223> OTHER INFORMATION: Antisense oligonucleotide

<400> SEQUENCE: 13
cagacatcct gaggtgtgtt ct                                             22

<210> SEQ ID NO 14
```

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 14
tgttcggttg ctgtgactgt                                                      20

<210> SEQ ID NO 15
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 15
atgcctgcca agccca                                                          16

<210> SEQ ID NO 16
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 16
cagccagccc tctgc                                                           15

<210> SEQ ID NO 17
<211> LENGTH: 16271
<212> TYPE: DNA
<213> ORGANISM: Homo sapiens

<400> SEQUENCE: 17
ggcttggggc agccgggtag ctcggaggtc gtggcgctgg gggctagcac cagcgctctg          60
tcgggaggcg cagcggttag gtggaccggt cagcggactc accggccagg gcgctcggtg         120
ctggaatttg atattcattg atccgggttt tatccctctt cttttttctt aaacattttt         180
ttttaaaact gtattgtttc tcgttttaat ttattttttgc ttgccattcc ccacttgaat        240
cgggccgacg gcttggggag attgctctac ttccccaaat cactgtggat tttggaaacc         300
agcagaaaga ggaaagaggt agcaagagct ccagagagaa gtcgaggaag agagagacgg         360
ggtcagagag agcgcgcggg cgtgcgagca gcgaaagcga caggggcaaa gtgagtgacc         420
tgcttttggg ggtgaccgcc ggagcgcggc gtgagccctc cccttgggga tcccgcagct         480
gaccagtcgc gctgacggac agacagacag acaccgcccc cagccccagc taccacctcc         540
tccccggccg gcggcggaca gtggacgcgg cggcgagccg cgggcagggg ccggagcccg         600
cgcccggagg cggggtggag ggggtcgggg ctcgcggcgt cgcactgaaa cttttcgtcc         660
aacttctggg ctgttctcgc ttcggaggag ccgtggtccg cgcggggaa gccgagccga         720
gcggagccgc gagaagtgct agctcgggcc gggaggagcc gcagccggag gaggggagg          780
aggaagaaga gaaggaagag gagaggggc cgcagtggcg actcggcgct cggaagccgg          840
gctcatggac gggtgaggcg gcggtgtgcg cagacagtgc tccagccgcg cgcgctcccc         900
aggccctggc ccgggcctcg ggccggggag gaagagtagc tcgccgaggc gccgaggaga         960
gcgggccgcc ccacagcccg agcggagag ggagcgcgag ccgcgccggc cccggtcggg         1020
cctccgaaac catgaacttt ctgctgtctt gggtgcattg gagccttgcc ttgctgctct        1080
acctccacca tgccaaggta gcggtcgtg ccctgctggc gccgcgggcc gctgcgagcg         1140
```

```
cctctcccgg ctggggacgt gcgtgcgagc gcgcgcgtgg gggctccgtg ccccacgcgg    1200
gtccatgggc accaggcgtg cggcgtcccc ctctgtcgtc ttaggtgcag ggggaggggg    1260
cgcgcgcgct aggtgggagg gtacccggag agaggctcac cgcccacgcg ggccctgccc    1320
acccaccgga gtcaccgcac gtacgatctg gccgaccag ccgagggcgg gagccggagg    1380
aggaggccga gggggctggg cttgcgttgc cgctgccggc tgaagtttgc tcccggccgc    1440
tggtcccgga cgaactggaa gtctgagcag cggggggcgg agccagagac cagtgggcag    1500
ggggtgctcg gaccttggac cgcgggaggg cagagagcgt ggaggggggca gggcgcagga    1560 gggagagggg gcttgctgtc actgccactc ggtctcttca gccctcgccg cgagtttggg    1620
aaaagttttg gggtggattg ctgcgggac ccccctccc tgctgggcca cctgcgccgc     1680
gccaaccccg cccgtccccg ctcgcgtccc gctcggtgcc cgcccteccc cgccggccg    1740 ggtgcgcgcg gcgcggagcc gattacatca gcccgggcct ggccggccgc gtgttcccgg    1800
agcctcggct gcccgaatgg ggagcccaga gtggcgagcg gcacccctcc ccccgccagc    1860
cctccgcggg aaggtgacct ctcgaggtag ccccagcccg gggatccaga gaaccatccc    1920
taccccttcc tactgtctcc agaccctacc tctgcccagt gctaggagga atttcctgac    1980
gccccttctc ttcacccatt tccttttag cctggagaga agccctgtc accccgctta     2040 ttttcatttc tctctgcgga gaagatccat ctaacccctt tctggcccca gagtccaggg    2100
aaaggatgat cactgtcaga agtcgtggcg cgggagccca ctgggcgctt tgtcacattc    2160
caccgaaagt cccgacttgg tgacagtgtg cttcccttcc ctcgccaaca gttccgagtg    2220
agctgtgctt tagctctcgt gggggtgggt caagggagga tttgaagagt cattgcccca    2280
ctttaccctt ttggagaaat ggcttgaaat ttgctgtgac acgggcagca tgggaatagt    2340
ccttcctgaa ccctggaaag gagctcctgc cagccttgca cacactttgt cctggtgaaa    2400
ggcagccctg gagcaggtgt tttttggaa ctccaaacct gcccacccaa cttgcttctg     2460
aaagggactc taaagggtcc cttccgctc ctctctgacg ccttccctca gccagaattc     2520
ccttggagag gaggcaagag gaaagccatg gacaggggtc gctgctaaca ccgcaagttc    2580
ctcagaccct ggcacaaagg ccttggctac aggcctccaa gtaggagga ggggaggag     2640 tggctgcctg gccacagtgt gaccttcaga ggcccccaga gaaggacacc tggcccctgc    2700
ctgcctagaa ccgcccctcc tgtgctccct ggccttggaa ggggtatgaa atttccgtcc    2760
cctttcctcc ttgggcccca ggaggagtgg agggtcccgg gagaatattg tcagggggaa    2820
ggcagggggt gtcatgggaa tgggtgaggg ggctgaggtg cagaatccag ggggtccctg    2880
caggagccgc agtggtaagc tgtccagctg gaagcctggt aactgttgtt ttctcttgag    2940
aggggcttcc tgtgaccttg gctgtctctg ggagcagggc tggggtacct gagtggggtg    3000
catttggggt gtgtgggaag gagagggaaa gaaagatgga cagtgggact ctcccctagc    3060
agggtctggt gttccgtagg ctagagtgcc cctctgctct gcgagtgctg ggcgggaggg    3120
gagttggtga gagctggaga cccccaggaa gggctggcag aagcctttcc ttttgggtgc    3180
tgtcaggtcc gcatgtcttg gcgtgttgac cttcacagct tctggcgagg ggaggaatga    3240
tctgatgcgg gtggggaggg ttagaggagg cctcaggcct aaggtggtgc agggggcccc    3300
ctaggggctg ggcagtgcca aggcataaaa gccttccctg gtccctggtg gcatttgaag    3360
gtgcccaggt gagaggggct tggcacctcc tcaccctggg aggagaaga aaccaggaa      3420 caggtaggag tgggagacag gtgaggcttt ggaaatctat tgaggctctg gagagatttg    3480
```

```
tgtagagagg aaaatgtggt tctcccccag ggtctcctcc tgggttttta ccctctaagc    3540
aacctgtggg catgctgggt tattcctaag gactagaaga gcttggatgg gggagggtgg    3600
ttggtgccct tcggtcctcg gcaccccct ccgtctccaa caccagctca ccctggtatt    3660
tgtcatgtca gcaggagaag gtcaccatgt gttttttctc gccctagtc cttccttcct    3720 gccccagtcc aaatttgtcc tcctatttga ccttaatact taccatggct ttggaccagg    3780
gaactagggg gatagtgaga gcagggagag ggaagtgtgg ggaaggtaca ggggacctcg    3840
acagtgaagc attctggggt tttcctcctg catttcgagc tccccagccc ccaacatctg    3900
gttagtcttt aacttcctcg ggttcataac catagcagtc caggagtggt gggcatattc    3960
tgtgcccgtg gggaccccg gttgtgtcct gttcgactca aagacttgg agaagccaga    4020 ggctgttggt gggagggaag tgaggaggga ggaggggctg ggtggctggg cctgtgcacc    4080
ccagcccctg cccatgccca tgccttgctc tctttctgtc ctcagtggtc ccaggctgca    4140
cccatggcag aaggaggagg gcagaatcat cacgaaggtg agtccccctg gctgttggat    4200
ggggttccct gtcctctcag gggatggtg gatggcctaa ttccttttc ttcagaactg    4260 tggggaggaa ggggaagggg cacaggaata taaggatcaa gaaagaaaga gctgggcacc    4320
acgaggttca ccctcagttt cgtgaggact ctccgctgtt caggtctctg ctagaagtag    4380
gacttgttgc cttttttcttc tgctctttcc agtaaaattt tatttggaga aggagtcgtg    4440
cgcacagagc aggaagacag tgttcaggga tcctaggtgt tgggggaagt gtcccttgtt    4500 tccctagct cccaggggag agtggacatt tagtgtcatt tcctatatag acatgtccca    4560
tttgtgggaa ctgtgaccct tcctgtgtga gctggaggca cagagggctc agcctaatgg    4620
gatctctcct cccttccctg gtttgcattc ctttgggggt ggagaaaacc ccatttgact    4680
atgttcgggt gctgtgaact tcctcccag gccagcagag ggctggctgt agctcccagg    4740
cgccccgccc cctgcccaa ccccgagtcc gcctgccttt tgttccgttg tggtttggat    4800
cctcccattt ctctggggac accctggctc tccccaccac tgactgtggc ctgtgctctc    4860
cacctctggg gagggaaggc cctggggtct tccttcccgc gagtttccct gacctaaatc    4920
tggcgtggct gggtagtggc cagcagtggt gatgcccagc ctgttctgcc tcctccttcc    4980
ccaccccagg agccctttcc ttggcctagg acctggcttc tcagccactg accggccccc    5040
tgcttccagt gcgccactta ccccttccag cttcccagtg gtctctggtc tgggagaggc    5100
aggacaaagg tctttgtttg ctggagaaaa ggttgtctgc gataaataag gaaaaccacg    5160
aaagcctggt tgttggagtg tacgtgtgtg ctcccccagg cagtggaggc cagccctcct    5220 tggagggcg gctgcctgat gaaggatgcg ggtgaggttc cccgcctcca cctcccatgg    5280
gacttgggga ttcattccaa ggggaagctt tttgggggaa ttcctacccc aggtcttttt    5340
accctcagtt accaaccct tgcccaggcc agaccttcct gctatcccct cctgggccac    5400
aagcctggcc ctcctctgtc ccaattgtga tgaaggggca gttcaaaact tcttgattag    5460
tcatcttctc ccctatcgac ttggctttaa aaaatgacct tttcagactt ctagtctcgt    5520
tcactctttt tgatgatgct ttgccgtaac ccttcgtggg tagagaagga ttctgtgccc    5580
attggtggtc tggataaaag aaatagagac ctcacaggaa gcagtggact ggcctgtttc    5640
cccactgttc tttctgtttt cacacctgtg gccttctccc caccttcttc ccaatcaacc    5700
tattgtgtac atagccccc tcattgtcct ttattcttct ggaaagcaga ccttggaggg    5760
aggagtgagg gggaggctca gctgtggtct ctggggggtg ggggtggga gctggggtgg    5820 aagtccacga agcatacact taagatgctt tggtgaagtt ctaaacttca tattacccag    5880
```

```
gctgaaaaaa gagcacttgt tcctagggct ggaaatggaa gccaaaacac caccttttc     5940 agcctgtttc agcatcttta gagatcagcc caacccactt acacagttga gcagagttgg    6000
aggcctagag aggggaggga ctggcccaag gtcataccaa ctcatggcca gagcctgggc    6060
ctcctcactg gccaggtgtt atttcttccc tctgggtagg gaacctattt cagggacagg    6120
attgctatgt ggtagtggtg gtggggtgcg ataggcgtgg caggctgggc cacaatttgg    6180
agtagtcatg ccagagtcct gcatttattt attctcaagg gccccgcctc tgtgcccag     6240 aattacccct tcatgctcca gtgcacccca ggcttcgtgg ccagcctggg aaactgtctc    6300
taccctggtc tcccttcaga tcagcttcta gaaatgtttc gtggctacag tggcagcact    6360
gttttttcca tgatgcaagc agtttgccct cttgggcggg ttatcagtg gctggcaggg     6420 ctggcacagc gtgtccgccc actgccacct gtgggttcca ggagggccca gcccctgtgc    6480
tgatgcccac caccttctca gctcatgtct ggggaagagg actggcaggg ggaaggtgc     6540 ctcctcctga aggtgcctc ctctgttttt gcctaatata ggcttgggaa cactttgatg     6600
tcagctaatt ctgactcctt tacttactag ctgtgcggcc ttggggcaac ttacttagcc    6660
tctttgagcc tcctgttccc catctgtaaa atggaatctc aatagtgtct aatagtacca    6720
tgtggagaaa cttgtgtgaa atgatagctg tggactactg tacacagtac tcaggatgta    6780
gtaagtgctc aataaacagc tgttggtatg gttgacgtta tggtagtggt tgtggggagg    6840
acgtaggaaa ctggagacta gcttggcaaa gctggctctt cctccttta gggaaagctt     6900 agagcatccc catggggtat acccatactc agactgtcct ctggcatcga ggttggccca    6960
ggattcagtt cagctgtcac agtgaggtgg cgggatcaga tgtggcaggc catgtccctt    7020
ggaacttgag tacatcgtgt gatctctgga atgaaaacag gccttcacca gtgttgatgg    7080
tggaaagctt agggaagtgc ttcaaacaca gtaggaggga cttacgttag atttttggaag   7140 gacttgcctg attcggaagc tccaaagagt ggcattacag agctgggtgg agagaggggc    7200
tagccatctt ttgtgtcgcc caccgggctc atgtgtcatc gcctctcatg cagtggtgaa    7260
gttcatggat gtctatcagc gcagctactg ccatccaatc gagaccctgg tggacatctt    7320
ccaggagtac cctgatgaga tcgagtacat cttcaagcca tcctgtgtgc ccctgatgcg    7380
atgcgggggc tgctgcaatg acgagggcct ggagtgtgtg cccactgagg agtccaacat    7440
caccatgcag gtgggcatct ttgggaagtg gggcaagggg gggataggga gggggtaac     7500 actttgggaa caggtggtcc caggtcgttt cctggctaga tttgccttgt ctggctcctg    7560
cccctgagtt gcacagggga ggtatggtgg ggtcttgcct tctgtggaga agatgcttca    7620
ttcccagccc aggttcccag caagccccaa ccatctcctt ctccctgatg gttgcccatg    7680
ggctcaggag gggacagatg gatgcctgtg tcaggagccc ctctctccct ctcttggaga    7740
gagtcctgag tgccccccct tcttgggggc tttgtttggg aagctggatg agcctggtcc    7800
atggagagtt taaaaagtct tttggtgtta cctggtaatg gggcacatct cagcccagat    7860
agggtgggag ggagctgtga acacaggga gggggttgct ttcgggtatc tactaggagt     7920
cagggtgaag cctagagagg atgaaagaag gggaggggat gggagtggt aagaacctag     7980 gatttgaatt cccagcctgg ccaacccttg cagccatgtc ttggcctcaa gtggaacaag    8040
ggctccttga ggccagcagg gttggggag ttgggtggg cctgagcctc tttcctgcta      8100
gagctcttgg tcctccctgc ctccaccacc catccctgct ctgcagaacc cctgggtgct    8160
gagtggcagg agcccaggg ttgtcccatc tgggtatggc tggctgggtc actaacctct     8220
```

| | | | | |
|---|---|---|---|---|
| gtgatctgct | tccttccttt | ccagattatg | cggatcaaac | ctcaccaagg | ccagcacata | 8280 |
| ggagagatga | gcttcctaca | gcacaacaaa | tgtgaatgca | ggtgaggatg | tagtcacgga | 8340 |
| ttcattatca | gcaagtggct | gcagggtgcc | tgatctgtgc | cagggttaag | catgctgtac | 8400 |
| tttttggccc | ccgtccagct | tcccgctatg | tgacctttgg | cattttactt | caatgtgcct | 8460 |
| cagtttctac | atctgtaaaa | tgggcacaat | agtagtatac | ttcatagcat | tgttataatg | 8520 |
| attaaacaag | ttatatatga | aaagattaaa | acagtgttgc | tccataataa | atgctgtttt | 8580 |
| tactgtgatt | attattgttg | ttatccctat | cattatcatc | accatcttaa | cccttccctg | 8640 |
| ttttgctctt | ttctctctcc | ctacccattg | cagaccaaag | aaagatagag | caagacaaga | 8700 |
| aaagtaagtg | gccctgactt | tagcacttct | ccctctccat | ggccggttgt | cttggtttgg | 8760 |
| ggctcttggc | tacctctgtt | gggggctccc | atagcctccc | tggtcaggg | acttggtctt | 8820 |
| gtgggggact | tgtggtggca | gcaacaatgg | gatggagcca | actccaggat | gatggctcta | 8880 |
| gggctagtga | gaaaacatag | ccaggagcct | ggcacttcct | ttggaaggga | caatgccttc | 8940 |
| tgggtctcca | gatcattcct | gaccaggact | tgctgtttcg | gtgtgtcagg | gggcactgtg | 9000 |
| gacactggct | cactggcttg | ctctaggaca | cccacagtgg | ggagagggag | tgggtggcag | 9060 |
| agaggccagc | ttttgtgtgt | cagaggaaat | ggcctctttt | ggtggctgct | gtgacggtgc | 9120 |
| agttggatgc | gaggccggct | ggaggtggt | ttctcagtgc | atgccctcct | gtaggcggca | 9180 |
| ggcggcagac | acacagccct | cttggccagg | agaaaaagt | tgaatgttgg | tcattttcag | 9240 |
| aggcttgtga | gtgctccgtg | ttaaggggca | ggtaggatgg | ggtgggggac | aaggtctggc | 9300 |
| ggcagtaacc | cttcaagaca | gggtgggcgg | ctggcatcag | caagagcttg | cagggaaaga | 9360 |
| gagactgaga | gagagcacct | gtgccctgcc | ctttccccca | caccatcttg | tctgcctcca | 9420 |
| gtgctgtgcg | gacattgaag | ccccaccag | gcctcaaccc | cttgcctctt | ccctcagctc | 9480 |
| ccagcttcca | gagcgagggg | atgcggaaac | cttccttcca | cccttggtg | ctttctccta | 9540 |
| aggggacag | acttgccctc | tctggtccct | tctcccctc | ctttcttccc | tgtgacagac | 9600 |
| atcctgaggt | gtgttctctt | gggcttggca | ggcatggaga | gctctggttc | tcttgaaggg | 9660 |
| gacaggctac | agcctgcccc | ccttcctgtt | tccccaaatg | actgctctgc | catgggaga | 9720 |
| gtaggggct | cgcctgggct | cggaagagtg | tctggtgaga | tggtgtagca | ggctttgaca | 9780 |
| ggctggggag | agaactccct | gccaagtacc | gcccaagcct | ctcctcccca | gacctcctta | 9840 |
| actcccaccc | catcctgctg | cctgcccagg | gctccaggac | acccagccct | gcctcccagt | 9900 |
| ccaggtcgtg | ctgagcaggc | tggtgttgct | cttggttccg | tgccagctcc | caaggtagcc | 9960 |
| gcttcccca | caccgggatt | cccagaggtt | ctgtcgcagt | tgcaaatgaa | ggcacaaggc | 10020 |
| ctgatacaca | gccctccctc | ccactcctgc | tccccatcca | ggcaggtctc | tgaccttctc | 10080 |
| cccaaagtct | ggcctacctt | ttatcacccc | cggaccttca | gggtcagact | tggacagggc | 10140 |
| tgctgggcaa | agagccttcc | ctcaggcttt | gcccctgcc | ggggactggg | agccactgtg | 10200 |
| agtgtggaga | cctttgggtc | ctgtgccctc | cacccagtct | cggcttccca | ccaaagcctt | 10260 |
| gtcaggggct | gggtttgcca | tcccatggtg | ggcagcgtga | ggagaagaaa | gagccatcga | 10320 |
| gtgcttgctg | cccagacacg | cctgtgtgcg | ccgcgcatg | cctccccaga | gaccacctgc | 10380 |
| ctcctgacac | ttcctccggg | aagcggccct | gtgtggcttt | gctttggtcg | ttccccatc | 10440 |
| cctgcccacc | ttaccacttc | ttttactccc | ccaccgccc | ccgctctctc | tctgtctctg | 10500 |
| tttttttatt | ttccagaaaa | tcagttcgag | gaaagggaaa | ggggcaaaaa | cgaaagcgca | 10560 |
| agaaatcccg | gtataagtcc | tggagcgtgt | acgttggtgc | ccgctgctgt | ctaatgccct | 10620 |

```
ggagcctccc tggcccccag tacaacctcc gcctgccatt ccctgtaacc ctgcctccct    10680
cccctggtcc ttccctggct ctcatcctcc tggcccgtgt ctctctctca ctctctcact    10740
ccactaattg gcaccaacgg gtagatttgg tggtggcatt gctggtccag ggttggggtg    10800 aatggggtg ccgacttggc ctggaggatt aagggagggg accctggctt ggctgggcac    10860
cgattttctc tcacccactg ggcactggtg gcgggcccat gttggcacag gtgcctgctc    10920
acccaactgg tttccattgc tctaggcttc tgcactcgtc tggaagctga gggtggtggg    10980
gagggcagac atgcccaag aagggctgtg aatgactgga ggcagcttgc tgaatgactc    11040
cttggctgaa ggaggagctt gggtgggatc agacaccatg tggcggcctc ccttcatctg    11100
gtggaagtgc cctggctcct cacggaggtg gggcctctgg aggggagccc cctattccgg    11160
cccaacccat ggcacccaca gaggcctcct tgcaggcag cctcttcctc tgggtcggag    11220
gctgtggtgg gccctgccct gggccctctg gccaccagcg gcctggcctg ggacaccgc    11280 ctccgggctt agcctcccat cacaccctac tttagcccac cttggtggaa gggcctggac    11340
atgagccttg cacggggaga aggtggcccc tgattgccat cccagcagg tgaagagtca    11400 aggcgtgctc cgatggggc aacagcagtt gggtccctgt ggcctgagac tcacccttgt    11460
ctcccagaga cacagcattg cccccttatgg cagcctctcc ctgcactctc tgcccgtctg    11520
tgcccgcctc ttcctgcggc aggtgtccta gccagtgctg cctctttccg ccgctctctc    11580
tgtcttttgc tgtagcgctc ggatccttcc agggcctggg ggctgaccgg ctgggtgggg    11640
gtgcagctgc ggacatgtta gggggtgttg catggtgatt tttttctct ctctctgctg    11700 atgctctagc ttagatgtct ttccttttgc cttttttgcag tccctgtggg ccttgctcag    11760
agcggagaaa gcatttgttt gtacaagatc cgcagacgtg taaatgttcc tgcaaaaaca    11820
cagactcgcg ttgcaaggcg aggcagcttg agttaaacga acgtacttgc aggttggttc    11880
ccagagggca agcaagtcag agaggggcat cacacagaga tggggagaga gagagagaaa    11940
gagagtgagc gagcgagcga gcgggagagc gcctgagagg ggccagctgc ttgctcagtt    12000
tctagctgcc tgcctggtga ctgctgcctt ctctgctttt aaggcccctg tggtgggctg    12060
caggcactgg tccagcctgg cggggcctgt tccgaggttg ccctggttgc ctgagtggta    12120
ggctggtgtg gcttagtgta gtggtgtgga cgcaagctgt gtgttgtgtc ctgtggtcct    12180
tctgctcata gtggctgttg gtcctgatgt tattactacc tctggtagta atgctgagaa    12240
gctgaaagcc gattccaggt gtggacaatg tcaacaaagc acagatgctc tcgctggggc    12300
cttgcctcgg cccttttgaag tctgcatggc tgggcttctc actcactcag tgtttcttgc    12360
tgggggaagg aattgagtct cccacttcag actgggcctc cctgaggaaa gggttgtgtc    12420
tccccactca gactgaggtt ccctgagggt agggctgtgt ctctcccctc cgacctgggc    12480
tccctgatag ggctgtctcc ccgctcagac tgaggctccc tcaggccagg gctatgtctc    12540
cctcctcaga ctggggctct gagggcaagg ggtctggctg ttcgtttagg atggggcact    12600
tttgcctaca cactgaagga gctgtagcat ccaagaatac tagatacctt taatcctcca    12660
ccagtcatgg tgacaacccc aagcagccca cacatttttca gtgccccca ggatgcgtgg    12720 agggaggggt ctgtgcccat tctcctgaca ttagcctgtg agctccgtaa gcccgggcct    12780
cgtttacgta cctttgtgag ccccgggcat ctgtacctct ttcctttgcc catactgggg    12840
accaaggaag tgtcaagtgc atgagtgaat gtgtgactca gttcagaggg tgaggtcagg    12900
agcacagggt cgggacaggt ggctggcatc ttttaatgcc ttagcttatg ttctttatac    12960
```

```
caacttggcc tgtgctcaga gtgagggagg ccctgggggt cagggtaagc gtcagtcagg    13020
gaggcaagac tttgtgggga tttcctagac agggccaagg cacccccagc tcaccccgag    13080
gctgtgttag ggaagtcctt ggagtgtctc ccctccccca gcaatgttct tgtggcttgt    13140
gtgtgctcag gggatgctgg gaaccaggcc tgggtagttg gtgtggggtg ctgtctgtct    13200
tggccctatg tgaaaccaag agggcgtata ttagtgctgg ggtgggggct ctgcctaact    13260
tcagggctgg atgaggggag tctcagttcc ccagggtcc ttgggaaaga taagggactt     13320
gacattttag ggttttagg tgattattct gctgatgggg gtttgtgtga agtgacctgg    13380
gagctaactg aagttactct aacctcccaa taccttacc caaccccaa gctggctgta     13440
tctgggaata tcagtttcca aaattggagg cttaggactc cgtttcgggg ctccccagaa    13500
gggtagggcc tgttctgcct ccttctcaca atcacccagg ggcagggca tgctgagaaa     13560
gttcttggag gcccccttg cttcagctgg agtagtgaag ccgccgaatt gtctctcccc    13620
atcctaagtg aagcagcata tttgaaagga aagacaacct gttacctggg cctgcaacct    13680
ccaggcagct caagagagat gaggcctaca gccacagtgg gaggggacat ggggaatgga    13740
gatggtccct caccttcctg gggcctcctg ctctacgcta ccccctcggg agcctcctgt    13800
ccccagggca ggcccttgcc attgttggtc acccggccaa gcctctctgc ctcaggcgtt    13860
ctcccagaag atctgcccac tctcttcccc acaccagccc ctagagactg aactgaaaac    13920
cctcctcagc agggagcctc ttctgattaa cttcatccag ctctggtcac ccatcagctc    13980
ttaaaatgtc aagtggggac tgttctttgg tatccgttca tttgttgctt tgtaaagtgt    14040
tcccatgtcc ttgtcttgtc tcaagtagat tgcaagctca ggagggtaga ctgggagccc    14100
ctgagtggag ctgctgctca ggccggggct ccctgagggc agggctgggg ctgttctcat    14160
actgggcgtt tctgccccag gaccacacct tcctgtcctc tctgctctta tggtgccgga    14220
ggctgcagtg acccaggggc ccccaggaat ggggaggccg cctgcctcat cgccaggcct    14280
cctcacttgg ccctaacccc agcctttgtt ttccatttcc ctcagatgtg acaagccgag    14340
gcggtgagcc gggcaggagg aaggagcctc cctcagggtt tcgggaacca gatctctcac    14400
caggaaagac tgatacagaa cgatcgatac agaaaccacg ctgccgccac cacaccatca    14460
ccatcgacag aacagtcctt aatccagaaa cctgaaatga aggaagagga gactctgcgc    14520
agagcacttt gggtccggag ggcgagactc cggcggaagc attcccggc gggtgaccca     14580
gcacggtccc tcttggaatt ggattcgcca ttttattttt cttgctgcta aatcaccgag    14640
cccggaagat tagagagttt tatttctggg attcctgtag acacacccac ccacatacat    14700
acatttatat atatatatat tatatatata taaaaataaa tatctctatt ttatatatat    14760
aaaatatata tattctttt ttaaattaac agtgctaatg ttattggtgt cttcactgga     14820
tgtatttgac tgctgtggac ttgagttggg aggggaatgt tcccactcag atcctgacag    14880
ggaagaggag gagatgagag actctggcat gatcttttt ttgtcccact tggtggggcc     14940
agggtcctct cccctgccca ggaatgtgca aggccaggga atgggggcaa atatgaccca    15000
gttttgggaa caccgacaaa cccagccctg cgctgagcc tctctacccc aggtcagacg     15060
gacagaaaga cagatcacag gtacaggat gaggacaccg ctctgacca ggagtttggg      15120
gagcttcagg acattgctgt gctttgggga ttccctccac atgctgcacg cgcatctcgc    15180
ccccaggggc actgcctgga agattcagga gcctgggcgg ccttcgctta ctctcacctg    15240
cttctgagtt gccaggagga ccactggcag atgtcccggc gaagagaaga gacacattgt    15300
tggaagaagc agcccatgac agctccccct cctgggactc gccctcatcc tcttcctgct    15360
```

```
ccccttcctg gggtgcagcc taaaaggacc tatgtcctca caccattgaa accactagtt    15420
ctgtcccccc aggagacctg gttgtgtgtg tgtgagtggt tgaccttcct ccatcccctg    15480
gtccttccct tcccttcccg aggcacagag agacagggca ggatccacgt gcccattgtg    15540
gaggcagaga aaagagaaag tgttttatat acggtactta tttaatatcc cttttaatt    15600 agaaattaaa acagttaatt taattaaaga gtagggtttt ttttcagtat tcttggttaa    15660
tatttaattt caactattta tgagatgtat cttttgctct ctcttgctct cttatttgta    15720 ccggttttg tatataaaat tcatgtttcc aatctctctc tccctgatcg gtgacagtca    15780
ctagcttatc ttgaacagat atttaatttt gctaacactc agctctgccc tccccgatcc    15840
cctggctccc cagcacacat tcctttgaaa taaggtttca atatacatct acatactata    15900
tatatatttg gcaacttgta tttgtgtgta tatatatata tatatgttta tgtatatatg    15960
tgattctgat aaaatagaca ttgctattct gttttttata tgtaaaaaca aaacaagaaa    16020
aaatagagaa ttctacatac taaatctctc tccttttta attttaatat ttgttatcat     16080
ttatttattg gtgctactgt ttatccgtaa taattgtggg gaaaagatat taacatcacg    16140
tctttgtctc tagtgcagtt tttcgagata ttccgtagta catatttatt tttaaacaac    16200
gacaaagaaa tacagatata tcttaaaaaa aaaaaagcat tttgtattaa agaatttaat    16260
tctgatctca a                                                         16271
```